US011020290B2

(12) United States Patent
Tsuji et al.

(10) Patent No.: US 11,020,290 B2
(45) Date of Patent: Jun. 1, 2021

(54) MATERIAL FOR ABSORBENT ARTICLE, METHOD FOR MANUFACTURING SAME, AND ABSORBENT ARTICLE USING SAME

(71) Applicant: KAO CORPORATION, Tokyo (JP)

(72) Inventors: Makoto Tsuji, Wakayama (JP); Takashi Itoi, Ichikai-machi (JP); Ichiro Mori, Saitama (JP); Satoshi Ishioka, Mibu-machi (JP); Katsushi Maeda, Haga-machi (JP)

(73) Assignee: KAO CORPORATION, Tokyo (JP)

( * ) Notice: Subject to any disclaimer, the term of this patent is extended or adjusted under 35 U.S.C. 154(b) by 155 days.

(21) Appl. No.: 15/544,440

(22) PCT Filed: Jan. 19, 2016

(86) PCT No.: PCT/JP2016/051346
§ 371 (c)(1),
(2) Date: Jul. 18, 2017

(87) PCT Pub. No.: WO2016/117523
PCT Pub. Date: Jul. 28, 2016

(65) Prior Publication Data
US 2018/0318149 A1    Nov. 8, 2018

(30) Foreign Application Priority Data

Jan. 19, 2015 (JP) .............................. JP2015-008165
Oct. 7, 2015 (JP) .............................. JP2015-199624

(51) Int. Cl.
*A61F 13/534* (2006.01)
*A61F 13/15* (2006.01)
(Continued)

(52) U.S. Cl.
CPC ............ *A61F 13/534* (2013.01); *A01N 33/12* (2013.01); *A01N 43/40* (2013.01); *A01N 57/02* (2013.01);
(Continued)

(58) Field of Classification Search
None
See application file for complete search history.

(56) References Cited

U.S. PATENT DOCUMENTS 6,136,771 A    10/2000  Taylor et al.
6,476,104 B1   11/2002  Nakamura et al.
(Continued)

FOREIGN PATENT DOCUMENTS

CN    1126585 A    7/1996
CN    1157300 A    8/1997
(Continued)

OTHER PUBLICATIONS

Table 3 of Scientific Committee on Consumer Safety, European Commission, Opinion on triclosan-antimicrobial resistance, Jun. 22, 2010. (Year: 2010).*
(Continued)

*Primary Examiner* — Melissa S Mercier
(74) *Attorney, Agent, or Firm* — Birch, Stewart, Kolasch & Birch, LLP

(57) ABSTRACT

The present invention discloses a material for an absorbent article, the material having an organic hydrophobic antimicrobial agent and a hydrophilic non-volatile organic solvent. The material for an absorbent article is preferably manufactured by a method having a step of applying an antimicrobial agent solution to a material for an absorbent article, the antimicrobial agent solution being formed by dissolving an organic hydrophobic antimicrobial agent in a hydrophilic non-volatile organic solvent. The present invention also
(Continued)

discloses an absorbent article in which the material for an absorbent article is used. The absorbent article is preferably manufactured by using a method having a step of making an absorbent core contain an antimicrobial agent solution formed by dissolving an organic hydrophobic antimicrobial agent in a hydrophilic non-volatile organic solvent.

5 Claims, 1 Drawing Sheet

(51) Int. Cl.
- A61F 13/472 (2006.01)
- B01J 20/26 (2006.01)
- A61F 13/84 (2006.01)
- A61L 15/24 (2006.01)
- A61F 13/53 (2006.01)
- A01N 33/12 (2006.01)
- A01N 43/40 (2006.01)
- A01N 57/02 (2006.01)

(52) U.S. Cl.
CPC ........ *A61F 13/15* (2013.01); *A61F 13/15617* (2013.01); *A61F 13/472* (2013.01); *A61F 13/8405* (2013.01); *A61L 15/24* (2013.01); *B01J 20/26* (2013.01); *B01J 20/267* (2013.01); *A61F 2013/530007* (2013.01); *A61F 2013/530481* (2013.01); *A61F 2013/8414* (2013.01); *A61L 2300/404* (2013.01)

(56) References Cited

U.S. PATENT DOCUMENTS

| | | | |
|---|---|---|---|
| 6,482,423 | B1 | 11/2002 | Beerse et al. |
| 2003/0020199 | A1 | 1/2003 | Kajikawa et al. |
| 2007/0274926 | A1 | 11/2007 | Fuls et al. |
| 2007/0274940 | A1 | 11/2007 | Fuls et al. |
| 2007/0275929 | A1 | 11/2007 | Fuls et al. |
| 2007/0280900 | A1 | 12/2007 | Fox et al. |
| 2007/0280901 | A1 | 12/2007 | Fuls et al. |
| 2007/0281999 | A1 | 12/2007 | Fox et al. |
| 2008/0145390 | A1 | 6/2008 | Taylor et al. |
| 2010/0198177 | A1* | 8/2010 | Yahiaoui ............ A61F 13/82 604/359 |
| 2010/0303869 | A1* | 12/2010 | Azad ............... A61L 15/46 424/400 |
| 2012/0070480 | A1 | 3/2012 | Amos et al. |
| 2012/0157302 | A1 | 6/2012 | Mitchell |
| 2016/0089464 | A1* | 3/2016 | Frankenbach ......... A61K 8/31 424/76.1 |

FOREIGN PATENT DOCUMENTS

| | | |
|---|---|---|
| CN | 1464826 A | 12/2003 |
| CN | 101460053 A | 6/2009 |
| EP | 0781804 A2 | 7/1997 |
| EP | 1197230 A1 | 4/2002 |
| JP | 9-248454 A | 9/1997 |
| JP | 11-501362 A | 2/1999 |
| JP | 2000-513408 A | 10/2000 |
| JP | 2002-540898 A | 12/2002 |
| JP | 2003-502353 A | 1/2003 |
| JP | 2005-295759 A | 4/2005 |
| JP | 2005-198701 A | 7/2005 |
| JP | 2006-191966 A | 7/2006 |
| JP | 2007-195936 A | 8/2007 |
| JP | 2007-254348 A | 10/2007 |
| JP | 2009-235199 A | 10/2009 |
| JP | 2010-540004 A | 12/2010 |
| JP | 2013-503219 A | 1/2013 |
| JP | 2013-540000 A | 10/2013 |
| JP | 2014-158509 A | 9/2014 |
| JP | 2016-104119 A | 6/2016 |
| RU | 2145880 C1 | 2/2000 |
| WO | WO 98/20916 A1 | 5/1998 |
| WO | WO-9938541 A1 * | 8/1999 ............ A01N 25/34 |

OTHER PUBLICATIONS

Propylene glycol definition by the New Encyclopedia accessed Aug. 30, 2019 (Year: 2019).*
Burke, Solubility Parameters: Theory and Application, The Oakland Museum of California, Aug. 1984 (Year: 1984).*
A Guide to Glycols, Dow Chemical Company, 2003 (Year: 2003).*
TGSC Information Sheet for piroctone olamine, accessed Aug. 30, 2019. (Year: 2019).*
Aerosil Catalogue, Dec. 1997, 7 pages, with partial English translation.
Buchholz et al., "Modern superabsorbent polymer technology," John Wiley & Sons, Inc., 1998, pp. 73-74 (4 pages total).
Ishiguro et al., "Polyethylene Glycols. X. Determination of Vapor Pressure of Polyethylene Glycols and Carbowax Compounds," Journal of the Pharmaceutical Society of Japan, vol. 75, No. 10, Oct. 1955, pp. 1188-1190 (5 pages total), with English abstract.
Solvent Handbook, Kodansha Scientific, edited by Asahara et al., Aug. 2001, pp. 847-850 (7 pages total), with partial English translation.
Extended European Search Report, dated Aug. 1, 2018, for European Application No. 16740130.6.
Partial English translation of WAKO, "Analytical Circle," Wako Pure Chemical, No. 64, Mar. 2012, p. 18.
International Search Report (PCT/SA/210) issued in PCT/JP2016/051346, dated Apr. 19, 2016.
Segur et al., "Viscosity of Glycerol and Its Aqueous Solutions," Industrial Engineering Chemistry, vol. 43, No. 9, Sep. 1, 1951, pp. 2117-2120.
Wako, "Analytical Circle," Wako Pure Chemical, No. 64, Mar. 2012, p. 18 (3 pages total).

* cited by examiner

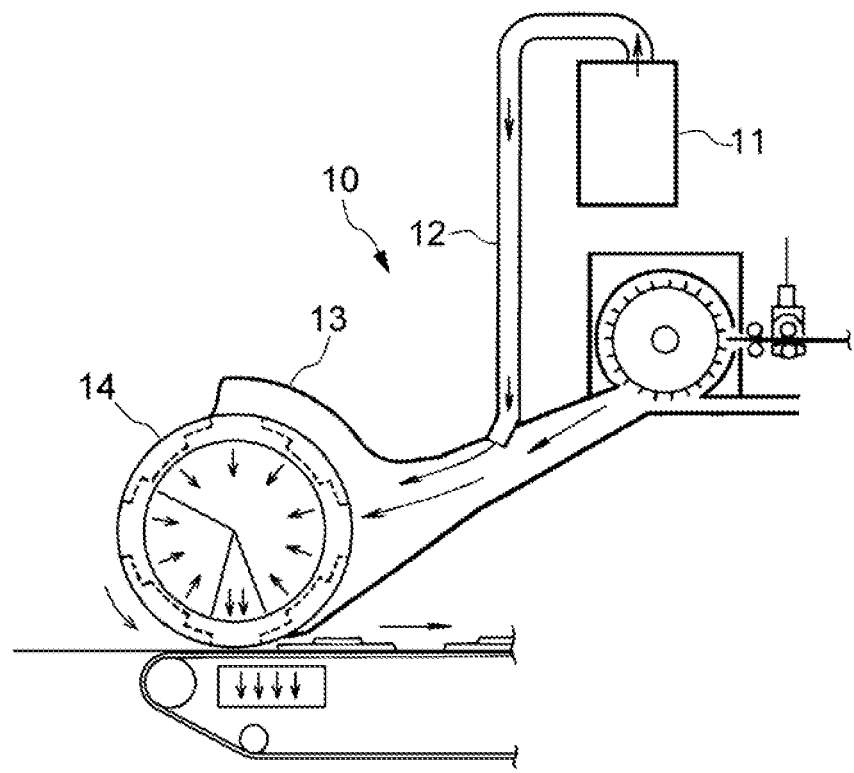

MATERIAL FOR ABSORBENT ARTICLE, METHOD FOR MANUFACTURING SAME, AND ABSORBENT ARTICLE USING SAME

TECHNICAL FIELD

The present invention relates to a material for an absorbent article. The present invention also relates to a method for manufacturing the material for an absorbent article, and an absorbent article in which the material is used.

BACKGROUND ART

In order to prevent the generation of an odor in a state in which an absorbent resin has absorbed excreta such as urine and menstrual blood, techniques are known which provide an antimicrobial agent to the absorbent resin. For example, Patent Literatures 1 and 2 disclose an antimicrobial hydrogel-forming absorbent polymer which contains a hydrogel-forming absorbent polymer and an antimicrobial agent and in which the hydrogel-forming absorbent polymer is coated with the antimicrobial agent.

Patent Literature 3 discloses an absorbent containing a mixture of crosslinking polymeric particles composed mainly of a (meth)acrylic acid (salt), a surface modifier having a surface tension of 40 to 80 dyn/cm, and water-insoluble particles having a volume average particle size of 1 to 500 nm. Patent Literature 3 also discloses that an antimicrobial agent such as benzalkonium chloride and chlorhexidine gluconate may be added to the absorbent. Patent Literature 4 discloses a process for producing super-absorbent member having a coating of an antimicrobial agent, the process including bringing a superabsorbent into contact with a solution containing the antimicrobial agent and a polyol concurrently with or immediately after bringing the superabsorbent into contact with a surface-crosslinking agent and prior to a curing stage in which surface crosslinking is completed.

Apart from the above-described techniques, techniques are also known which have an antimicrobial effect on the skin of a user by using paper, such as tissue paper, to which an antimicrobial agent has been provided. For example, Patent Literature 5 discloses an absorbent article in which an antimicrobial agent and activated carbon are disposed between an absorbent core and a topsheet. Patent Literature 6 proposes tissue paper to which an antimicrobial agent has been provided, in order to reduce skin irritation during nose-blowing. Patent Literature 7 proposes an antimicrobial cleansing wipe for cleaning the skin surface and controlling the proliferation and viability of bacteria. This cleansing wipe contains an antimicrobial agent.

CITATION LIST

Patent Literatures

Patent Literature 1: JP H11-501362A
Patent Literature 2: JP 2000-513408A
Patent Literature 3: JP 2005-95759A
Patent Literature 4: JP 2010-540004A
Patent Literature 5: JP 2006-191966A
Patent Literature 6: JP 2007-195936A
Patent Literature 7: JP 2002-540898A

SUMMARY OF INVENTION

According to the techniques disclosed in Patent Literatures 1 and 2, the antimicrobial agent is dissolved in an organic solvent prior to the hydrogel-forming absorbent polymer being coated with the antimicrobial agent. If an appropriate organic solvent is not chosen, a distinctive odor of the organic solvent may be generated, a problem concerning the safety of the human body may arise, and there may be concern about being safe from ignition and explosion. With respect to the technique disclosed in Patent Literature 3, how the antimicrobial agent is added is not clearly described. Depending on the method of addition, the antimicrobial agent may non-uniformly adhere to the cross-linking polymeric particles, and there is a possibility that a desired effect cannot be obtained. With the technology disclosed in Patent Literature 4, there is a possibility that the antimicrobial agent will deteriorate due to heat that is applied while the surface-crosslinking agent is cured. Moreover, depending on the type of the polyol, the antimicrobial agent may not be dissolved, and thus, there is a possibility that the antimicrobial agent will not uniformly adhere to the surface of the superabsorbent.

Meanwhile, with the techniques disclosed in Patent Literatures 5 to 7, the antimicrobial effect can be exhibited to some extent. However, the antimicrobial effect is exhibited only at the site to which the antimicrobial agent has been provided, and therefore, there is a demand for an even higher antimicrobial effect to be exhibited. Moreover, Patent Literatures 5 to 7 do not disclose a method for applying the antimicrobial agent such that a high antimicrobial effect can be exhibited.

Solution to Problem

The present invention provides a material for an absorbent article, the material having an organic hydrophobic antimicrobial agent and a hydrophilic non-volatile organic solvent.

The present invention also provides an absorbent article in which the material for an absorbent article is used The present invention also provides a method for manufacturing a material for an absorbent article, the method having a step of applying an antimicrobial agent solution to a material for an absorbent article, the antimicrobial agent solution being formed by dissolving an organic hydrophobic antimicrobial agent in a hydrophilic non-volatile organic solvent.

The present invention also provides a method for manufacturing an absorbent article, the method having a step of making an absorbent core contain an antimicrobial agent solution formed by dissolving an organic hydrophobic antimicrobial agent in a hydrophilic non-volatile organic solvent.

Furthermore, the present invention provides an absorbent article including an absorbent core containing an organic hydrophobic antimicrobial agent and a hydrophilic non-volatile organic solvent.

BRIEF DESCRIPTION OF DRAWINGS

FIG. 1 schematically shows a state in which an absorbent resin composition obtained by using a manufacturing method of the present invention is pneumatically conveyed.

DESCRIPTION OF EMBODIMENTS

The present invention relates to an improvement in an article containing an antimicrobial agent. More specifically, the present invention relates to an enhancement of the antimicrobial properties of a material for an absorbent article, and an absorbent article, compared with conventional ones. Moreover, the present invention relates to a method with which a material for an absorbent article, and an absorbent article, that have high antimicrobial properties can be easily manufactured.

Hereinafter, the present invention will be described based on preferred embodiments thereof. The present invention relates to a material for an absorbent article. The material for an absorbent article of the present invention encompasses a wide range of materials that are known in the art as materials constituting absorbent articles. Typical examples of the material for an absorbent article include, but are not limited to, sheet materials, absorbent materials, and elastic materials. In the case where the material for an absorbent article is a sheet material, the sheet material may be, for example, a topsheet, a backsheet, a cover sheet that covers an absorbent core, a sublayer sheet that is located directly under the topsheet, or the like. In the case where the material for an absorbent article is an absorbent material, the absorbent material may be a liquid-absorbent fiber such as pulp, an absorbent resin such as a superabsorbent polymer, or the like. In the case where the material for an absorbent article is an elastic material, the elastic material may be, for example, a filamentous elastic member, a band-like elastic member, or the like.

In the case where the material for an absorbent article is an absorbent resin, the material for an absorbent article is made from an absorbent resin composition. This absorbent resin composition contains at least an absorbent resin and an antimicrobial agent as essential ingredients. Depending on manufacturing conditions, the composition may also contain an organic solvent as an ingredient in addition to the absorbent resin and the antimicrobial agent. Furthermore, the composition may also contain inorganic fine particles as an ingredient.

In the absorbent resin composition, the antimicrobial agent can be present in a state in which it adheres to the surface of the absorbent resin. Similarly, the organic solvent and the inorganic fine particles can also be present in a state in which they adhere to the surface of the absorbent resin.

A macromolecular material that swells upon absorbing water and is capable of retaining water may be used as the absorbent resin. Such macromolecular materials are known in the art. Specifically, a macromolecular material obtained by polymerizing at least one monomer selected from the following monomers may be used. The macromolecular material may also be subjected to crosslinking treatment as necessary. The method of polymerization is not limited to a specific method, and various commonly known methods such as reversed-phase suspension polymerization and aqueous solution polymerization can be used. Then, the obtained polymer may be subjected to pulverization, sizing, and other operations as necessary, and may also be subjected to surface treatment as necessary.

Preferably, the above-described monomers are water-soluble monomers having a polymerizable unsaturated group. Specific examples thereof include vinyl monomers having a polymerizable unsaturated group, such as olefinically unsaturated carboxylic acids or salts thereof, olefinically unsaturated carboxylic acid esters, olefinically unsaturated sulfonic acids or salts thereof, olefinically unsaturated phosphoric acids or salts thereof, olefinically unsaturated phosphoric acid esters, olefinically unsaturated amines, olefinically unsaturated ammonium salts, and olefinically unsaturated amides.

Examples of the olefinically unsaturated carboxylic acids or salts thereof include unsaturated carboxylic acids, such as acrylic acid, methacrylic acid, maleic acid, and fumaric acid, alkali metal salts thereof, ammonium salts thereof, and the like.

Examples of the olefinically unsaturated carboxylic acid esters include 2-hydroxyethyl (meth)acrylate, 2-hydroxypropyl (meth)acrylate, methoxy polyethylene glycol (meth)acrylate, polyethylene glycol mono(meth)acrylate, phenoxy polyethylene glycol (meth)acrylate, and the like.

Examples of the olefinically unsaturated sulfonic acids or salts thereof include vinylsulfonic acid, allylsulfonic acid, styrenesulfonic acid, 2-(meth)acrylamide-2-methylpropanesulfonic acid, 2-(meth)acryloylethanesulfonic acid, and 2-(meth)acryloylpropanesulfonic acid or a salt thereof.

Examples of the olefinically unsaturated phosphoric acids or salts thereof include (meth)acryloyl(poly)oxyethylene phosphoric acid ester or a salt thereof.

Examples of the olefinically unsaturated amines include N,N-dimethylaminoethyl (meth)acrylate, N,N-diethylaminoethyl (meth)acrylate, N,N-dimethylaminopropyl (meth)acrylate, and N,N-dimethylaminopropyl (meth)acrylamide.

Examples of the olefinically unsaturated ammonium salts include quaternary ammonium salts of the above-described olefinically unsaturated amines.

Examples of the olefinically unsaturated amides include (meth)acrylamide, derivatives of (meth)acrylamide, such as methyl (meth)acrylamide, N-ethyl (meth)acrylamide, N-propyl (meth)acrylamide, N-isopropyl (meth)acrylamide, and N,N-dimethyl (meth)acrylamide, and vinyl methylacetamide.

Specific examples of other monomers include nonionic, hydrophilic group-containing unsaturated monomers such as vinylpyridine, N-vinylpyrrolidone, N-acryloylpiperidine, N-acryloylpyrrolidine, and N-vinylacetamide.

It should be noted that, in the present specification, "(meth)acrylate" means acrylate or methacrylate, "(meth)acrylamide" means acrylamide or methacrylamide, and "(meth)acryloyl" means acryloyl or methacryloyl.

Specific examples of the absorbent resin include starch and crosslinked carboxylmethylated cellulose, as well as polyacrylic acid, salts thereof, and polyacrylic acid salt graft polymers, such as polymers or copolymers of acrylic acid or alkali metal salts of acrylic acid. A sodium salt can be preferably used as a polyacrylic acid salt. Moreover, copolymers obtained by copolymerizing acrylic acid with comonomers such as maleic acid, itaconic acid, acrylamide, 2-acrylamide-2-methylpropanesulfonic acid, 2-(meth)acryloylethanesulfonic acid, 2-hydroxyethyl(meth)acrylate, and styrenesulfonic acid without reducing the performance of the absorbent resin may also be preferably used.

There is no limitation on the shape of the absorbent resin. For example, any shape such as a spherical shape, a clump shape, the shape of a bunch of grapes, and a fibrous shape can be used. The average particle size of the absorbent resin is preferably not less than 10 μm and more preferably not less than 100 μm, and also preferably not more than 1000 μm and more preferably not more than 800 μm. More specifically, the average particle size of the absorbent resin is preferably between 10 μm and 1000 μm inclusive and more preferably between 100 μm and 800 μm inclusive.

An organic compound is used as the antimicrobial agent. The reason for this is that organic antimicrobial agents have a high antimicrobial effect compared with inorganic antimicrobial agents such as zinc oxide and silver-containing antimicrobial agents. Moreover, a hydrophobic antimicrobial agent is used as the antimicrobial agent. The reason for this is that hydrophobic antimicrobial agents have low skin irritancy compared with hydrophilic antimicrobial agents.

Hydrophilic antimicrobial agents are likely to penetrate the skin because of their hydrophilicity, and are therefore likely to irritate the skin. In contrast, it is unlikely for hydrophobic antimicrobial agents to penetrate the skin because of their hydrophobicity, and thus, hydrophobic antimicrobial agents are likely to remain on the surface of the skin. Therefore, hydrophobic antimicrobial agents are unlikely to irritate the skin. A hydrophobic antimicrobial agent refers to an antimicrobial agent having a solubility in water at 25° C. of preferably not more than 40 g, more preferably not more than 10 g, and even more preferably not more than 1 g. The solubility of antimicrobial agents can be measured using the following method. A sufficiently dried antimicrobial agent is put into 100 g of pure water at 25° C. and dissolved therein through stirring with a stirrer or a shaker. An input amount of the antimicrobial agent immediately less than an input amount at which the antimicrobial agent cannot be completely dissolved even after stirring for one hour is used as the solubility of that antimicrobial agent in water at 25° C.

As described above, an organic hydrophobic antimicrobial agent is used in the present invention. Preferably, organic compounds represented by formula (1) or (2) below, for example, are used as the organic hydrophobic antimicrobial agent, because these organic compounds have a high antimicrobial effect and low skin irritancy. These organic compounds may be used alone or may be used in combination of two or more.

[Chem. 1]

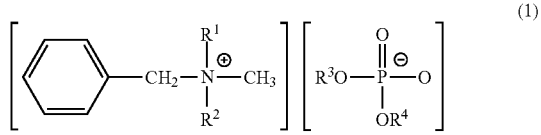

(1)

wherein $R^1$ and $R^2$ each independently represent a methyl group, an ethyl group, a linear or branched alkyl group having 6 to 24 carbon atoms or a linear or branched alkenyl group having 6 to 24 carbon atoms; and
one of $R^3$ and $R^4$ represents a linear or branched alkyl group having 6 to 30 carbon atoms, a linear or branched alkenyl group having 6 to 30 carbon atoms or an alkyl-alkylene oxide group (an alkyl moiety and an alkylene moiety in the group may be linear or may be branched), and the other of $R^3$ and $R^4$ represents a hydrogen atom, a methyl group, or an ethyl group, or alternatively, $R^3$ and $R^4$ each independently represent a linear or branched alkyl group having 6 to 30 carbon atom, a linear or branched alkenyl group having 6 to 30 carbon atoms, or an alkyl-alkylene oxide group (an alkyl moiety and an alkylene moiety in the group may be linear or may be branched).

In the organic hydrophobic antimicrobial agent represented by formula (1), except when $R^1$ and $R^2$ each represent a methyl group or an ethyl group, $R^1$ and $R^2$ each independently have preferably 6 or more carbon atoms, more preferably 8 or more carbon atoms, and even more preferably 10 or more carbon atoms, and also preferably 24 or less carbon atoms, more preferably 22 or less carbon atoms, and even more preferably 20 or less carbon atoms. Specifically, $R^1$ and $R^2$ each independently have preferably 6 to 24 carbon atoms, more preferably 8 to 22 carbon atoms, and even more preferably 10 to 20 carbon atoms.

In the organic hydrophobic antimicrobial agent represented by formula (1), except when $R^3$ and $R^4$ each represent a methyl group or an ethyl group, $R^3$ and $R^4$ each independently have preferably 6 or more carbon atoms, more preferably 8 or more carbon atoms, and even more preferably 10 or more carbon atoms, and also preferably 30 or less carbon atoms, more preferably 24 or less carbon atoms, and even more preferably 22 or less carbon atoms. Specifically, $R^3$ and $R^4$ each independently have preferably 6 to 30 carbon atoms, more preferably 8 to 24 carbon atoms, and even more preferably 10 to 22 carbon atoms.

In the organic hydrophobic antimicrobial agent represented by formula (1), in the case where $R^3$ and/or $R^4$ is an alkyl-alkylene oxide group, the alkyl group of the alkyl-alkylene oxide group has preferably 6 or more carbon atoms and more preferably 8 or more carbon atoms, and also preferably 24 or less carbon atoms and more preferably 22 or less carbon atoms. Specifically, the alkyl group has preferably 6 to 24 carbon atoms and more preferably 8 to 22 carbon atoms. The alkylene group of the alkyl-alkylene oxide group has more preferably 2 or more carbon atoms, and also preferably 6 or less carbon atoms and more preferably 4 or less carbon atoms. Specifically, the alkylene group has preferably 2 to 6 carbon atoms and more preferably 2 to 4 carbon atoms.

[Chem. 2]

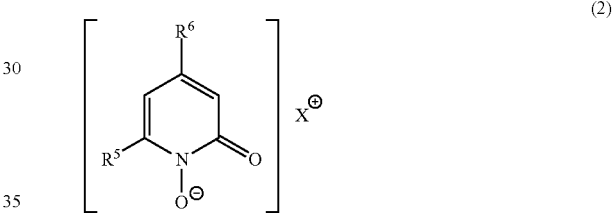

(2)

wherein $R^5$ represents a linear or branched alkyl group having 1 to 30 carbon atoms, a linear or branched alkenyl group having 1 to 30 carbon atoms, an optionally linear or branched cycloalkyl group, an optionally linear or branched aryl group, or an alkyl-alkylene oxide group (an alkyl moiety and an alkylene moiety in the group may be linear or may be branched);
$R^6$ represents a hydrogen atom, a linear or branched alkyl group having 1 to 6 carbon atoms, a linear or branched alkenyl group having 1 to 6 carbon atoms, an optionally linear or branched cycloalkyl group, a phenyl group, or a benzyl group; and
$X^+$ represents an alkali metal ion, an alkaline earth metal ion, an ammonium ion, or a divalent to tetravalent cation (excluding an alkaline earth metal ion).

In the organic hydrophobic antimicrobial agent represented by formula (2), $R^5$ has preferably 1 or more carbon atom, more preferably 3 or more carbon atoms, and even more preferably 6 or more carbon atoms, and also preferably 30 or less carbon atoms, more preferably 24 or less carbon atoms, and even more preferably 22 or less carbon atoms. Specifically, $R^5$ has preferably 1 to 30 carbon atoms, more preferably 3 to 24 carbon atoms, and even more preferably 6 to 22 carbon atoms.

In the organic hydrophobic antimicrobial agent represented by formula (2), in the case where $R^5$ is a cycloalkyl group, the cycloalkyl group has preferably 6 or more carbon atoms and more preferably 7 or more carbon atoms, and also preferably 30 or less carbon atoms and more preferably 24 or less carbon atoms. Specifically, the cycloalkyl group has preferably 6 to 30 carbon atoms and more preferably 7 to 24 carbon atoms.

In the organic hydrophobic antimicrobial agent represented by formula (2), in the case where $R^5$ is an aryl group, the aryl group is preferably a phenyl group, a phenyl group substituted with an alkyl group having 1 to 18 carbon atoms, a benzyl group, a benzyl group substituted with an alkyl group having 1 to 18 carbon atoms, or a phenoxyalkyl group having 7 to 24 carbon atoms.

In the organic hydrophobic antimicrobial agent represented by formula (2), in the case where $R^5$ is an alkyl-alkylene oxide group, the alkyl group of the alkyl-alkylene oxide group has more preferably 6 or more carbon atoms, and also preferably 24 or less carbon atoms and more preferably 22 or less carbon atoms. Specifically, the alkyl group has preferably 6 to 24 carbon atoms and more preferably 6 to 22 carbon atoms. The alkylene group of the alkyl-alkylene oxide group has more preferably 2 or more carbon atoms, and also preferably 6 or less carbon atoms and more preferably 4 or less carbon atoms. Specifically, the alkylene group has preferably 2 to 6 carbon atoms and more preferably 2 to 4 carbon atoms.

In the organic hydrophobic antimicrobial agent represented by formula (2), $R^6$ has preferably 1 or more carbon atoms, and also preferably 6 or less carbon atoms and more preferably 4 or less carbon atoms. Specifically, $R^6$ has preferably 1 to 6 carbon atoms and more preferably 1 to 4 carbon atoms.

In the organic hydrophobic antimicrobial agent represented by formula (2), in the case where $R^6$ is a cycloalkyl group, the cycloalkyl group is more preferably a cyclopentyl group or a cyclohexyl group.

In the organic hydrophobic antimicrobial agent represented by formula (2), in the case where $X^+$ is an alkali metal ion, examples thereof include a lithium ion, a sodium ion, and a potassium ion. In the case where $X^+$ is an alkaline earth metal ion, examples thereof include a magnesium ion, a calcium ion, and a strontium ion. In the case where $X^+$ is a divalent to tetravalent cation, examples thereof include protonated salts of amines (amines to which $H^+$ is attached) such as ethanolamine, diethanolamine, triethanolamine, N-substituted ethanolamine, N-substituted diethanolamine, trishydroxyaminomethane, guanidine, ethylenediamine, hexamethylenediamine, and hexamethylenetetramine.

A specific example of the organic hydrophobic antimicrobial agent represented by formula (1) is benzalkonium cetyl phosphate. An antimicrobial agent marketed by Kao Corporation under the trade name SANISOL P can be used as benzalkonium cetyl phosphate. On the other hand, a specific example of the organic hydrophobic antimicrobial agent represented by formula (2) is a 1-hydroxy-4-methyl-6-(2,4,4-trimethylpentyl)-2(1H)-pyridone monoethanolamine salt [1-Hydroxy-4-methyl-6-(2,4,4-trimethyl-pentyl)-2(1H)-pyridone; combination with 2-aminoethanol (1:1)] (CAS registry number: 68890-66-4, synonym: piroctone olamine). This antimicrobial agent is represented by formula (2A) and marketed by Clariant under the trade name Piroctone Olamine.

[Chem. 3]

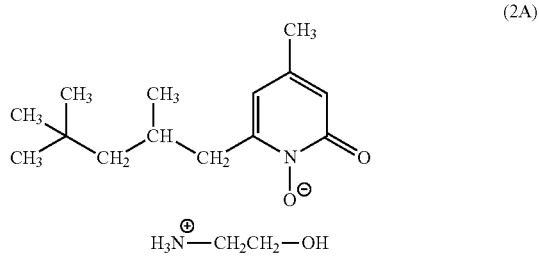

(2A)

An example of an organic hydrophobic antimicrobial agent other than those described above is 5-chloro-2-[2,4-dichlorophenoxy]phenol. This compound is also called triclosan.

In order to cause the organic hydrophobic antimicrobial agent to adhere to the absorbent resin, in the present invention, it is preferable to adopt a step of forming an antimicrobial agent solution by dissolving the organic hydrophobic antimicrobial agent in an organic solvent, and mixing the antimicrobial agent solution with the absorbent resin. Mixing the antimicrobial agent solution with the absorbent resin makes it possible for the organic hydrophobic antimicrobial agent to uniformly adhere to the absorbent resin. Preferably, the antimicrobial agent solution is a solution in which the organic hydrophobic antimicrobial agent is completely dissolved. In the case where an undissolved portion of the organic hydrophobic antimicrobial agent is present in the antimicrobial agent solution, if such an antimicrobial agent solution is mixed with the absorbent resin, the organic hydrophobic antimicrobial agent may non-uniformly adhere to the absorbent resin.

The above-described method may have a surface-cross-linking step of crosslinking a surface of the absorbent resin prior to performing the step of mixing the antimicrobial agent solution with the absorbent resin. Desired water-absorption performance of the absorbent resin can be obtained by performing the surface-crosslinking step.

It is preferable the above-described organic solvent is a liquid at 25° C. An organic solvent in which the organic hydrophobic antimicrobial agent can be dissolved is used as the organic solvent. In particular, an organic solvent in which the solubility of the organic hydrophobic antimicrobial agent is preferably not less than 5 mass %, more preferably not less than 10 mass %, and even more preferably not less than 15 mass % is advantageously used. A solubility of X mass % as used herein means that X g or more of the organic hydrophobic antimicrobial agent dissolves in 100 g of the organic solvent. In the case where the solubility of the organic hydrophobic antimicrobial agent varies depending on the temperature, it is preferable that the solubility at a temperature at which the antimicrobial agent solution is mixed with the absorbent resin is as described above.

From the standpoint of ensuring sufficient solubility of the organic hydrophobic antimicrobial agent, the solubility parameter of the organic solvent is preferably not less than 12, more preferably not less than 13, even more preferably not less than 13.5, and yet more preferably not less than 14. Also, the solubility parameter is preferably not more than 28, more preferably not more than 27, even more preferably not more than 26, and yet more preferably not more than 25. Specifically, the solubility parameter is preferably between 12 and 28 inclusive, more preferably between 13 and 27 inclusive, even more preferably between 13.5 and 26 inclusive, and yet more preferably between 14 and 25 inclusive. The solubility parameter is calculated by using the Fedors' method [R. F. Fedors, Polym. Eng. Sci., 14, 147 (1974)] and expressed in units of $(cal/cm^3)^{1/2}$. The solubility parameter is one of the indices that indicate the affinity between the organic hydrophobic antimicrobial agent and the organic solvent, and the closer the solubility parameter values of the organic hydrophobic antimicrobial agent and the organic solvent, the higher the compatibility therebetween.

The solubility parameter δ of the organic solvent is obtained by using the following equation:

$$\delta = (\Delta E/V)^{1/2} \; (cal/cm^3)^{1/2}$$

wherein ΔE represents evaporation energy, and V represents molar volume.

In the case where two or more organic solvents are used, it is preferable that the solubility parameter $\delta_{mix}$ of the mixture shown below is not less than the above-described values:

$$\delta_{mix} = \Sigma \delta_i \varphi_i \ (cal/cm^3)^{1/2}$$

wherein $\delta_i$ represents the solubility parameter of each of the organic solvents constituting the mixture, and $\varphi$ represents the volume fraction of that component.

It is preferable that the organic solvent has low volatility. If a highly volatile organic solvent is used, the organic solvent may be volatilized in the manufacturing process of the absorbent resin composition, and therefore it is necessary to add an air exhauster to the manufacturing facility. In contrast, if an organic solvent having low volatility is used, it is unnecessary to add such a device. Moreover, a highly volatile organic solvent may ignite or explode, and therefore it is necessary to add an explosion-proof device to a manufacturing device; however, if an organic solvent having low volatility is used, it is unnecessary to add such a device. Thus, the use of an organic solvent having low volatility makes it possible to leave the organic solvent remaining in the absorbent resin composition after mixing of the antimicrobial agent solution with the absorbent resin.

From the above-described point of view, the vapor pressure of the organic solvent at 25° C. is preferably not less than 30 Pa, more preferably not less than 20 Pa, even more preferably not less than 15 Pa, and yet more preferably not less than 10 Pa.

From the standpoint of ensuring security in the manufacturing process of the absorbent resin composition, it is preferable that the organic solvent has a high flash point. The use of an organic solvent having a high flash point makes it possible to manufacture the absorbent resin composition at a basic facility. Specifically, the flash point of the organic solvent is preferably not less than 100° C., more preferably not less than 105° C., even more preferably not less than 110° C., and yet more preferably not less than 115° C. The flash point refers to the liquid temperature at which a combustible vapor reaches the lowest concentration value at which it explodes, and is measured in conformity with the Cleveland open-cup flash point measurement test specified in HS K2265.

From the standpoint of providing favorable handleability of the organic solvent in the manufacturing process of the absorbent resin composition, it is preferable that the organic solvent has a low molecular weight. If the organic solvent has a high molecular weight, the organic solvent tends to have an increased viscosity and accordingly poor handleability. Specifically, the molecular weight of the organic solvent is preferably less than 200, more preferably less than 150, even more preferably less than 100, and yet more preferably less than 91.

From the same standpoint as that with respect to the molecular weight, it is preferable that the organic solvent has an appropriate viscosity and accordingly favorable handleability. If the organic solvent has an excessively high viscosity, the organic solvent tends to have poor handleability. Conversely, if the organic solvent has an excessively low viscosity, it is hard for the organic solvent to become fixed to the absorbent resin, and therefore it is difficult to uniformly provide the organic hydrophobic antimicrobial agent to the absorbent resin. From these points of view, the viscosity of the organic solvent at 25° C. is preferably not less than 5 mPa·s, more preferably not less than 10 mPa·s, even more preferably not less than 30 mPa·s, and yet more preferably not less than 60 mPa·s. Also, the viscosity of the organic solvent at 25° C. is preferably not more than 1500 mPa·s, more preferably not more than 500 mPa·s, even more preferably not more than 300 mPa·s, and yet more preferably not more than 90 mPa·s. Specifically, the viscosity of the organic solvent at 25° C. is preferably between 5 mPa·s and 1500 mPa·s inclusive, more preferably between 10 mPa·s and 500 mPa·s inclusive, even more preferably between 30 mPa·s and 300 mPa·s inclusive, and yet more preferably between 60 mPa·s and 90 mPa·s inclusive. The viscosity of the organic solvent can be measured by using a Model B or Model TVB viscometer manufactured by Toki Sangyo Co., Ltd at 25° C.

It should be noted that an organic solvent is said to be hydrophilic when the solubility of that organic solvent in water at 25° C. is not less than 10 mass %. The solubility of an organic solvent can be measured by using the following method: An organic solvent is put into 100 g of pure water at 25° C. and dissolved therein through stirring with a stirrer or a shaker, and an input amount of the organic solvent that is immediately less than an input amount at which the organic solvent cannot be completely dissolved even after stirring for 10 minutes is used as the solubility of that organic solvent in water at 25° C.

Examples of preferred compounds that can be used as the organic solvent include water-soluble organic solvents such as polyhydric alcohols including dihydric alcohols (diols), trihydric alcohol (triols), tetrahydric or higher polyhydric alcohols, and the like. It is preferable that the alkyl group of these polyhydric alcohols has 2 or more carbon atoms. Also, the alkyl group has preferably 18 or less carbon atoms, more preferably 10 or less carbon atoms, and even more preferably 4 or less carbon atoms. Specifically, the alkyl group has preferably 2 to 18 carbon atoms, more preferably 2 to 10 carbon atoms, and even more preferably 2 to 4 carbon atoms.

In particular, among the polyhydric alcohols, lower dihydric alcohols having 2 to 4 carbon atoms are preferably used. Specifically, it is preferable to use at least one hydrophilic organic solvent selected from the group consisting of ethylene glycol, propylene glycol, and butylene glycol. These hydrophilic organic solvents are highly safe to use on the human body, do not generate odors, do not require a removing step, and are less likely to ignite or explode. 1,2-Propylene glycol and 1,3-propylene glycol can be used as the propylene glycol. 1,3-Butylene glycol, 1,4-butylene glycol, and 2,3-butylene glycol can be used as the butylene glycol.

The concentration of the organic hydrophobic antimicrobial agent in the antimicrobial agent solution is preferably not less than 0.5 mass %, more preferably not less than 1 mass %, even more preferably not less than 3 mass %, and yet more preferably not less than 5 mass %. Also, the concentration of the organic hydrophobic antimicrobial agent in the antimicrobial agent solution is preferably not more than 50 mass %, more preferably not more than 35 mass %, even more preferably not more than 25 mass %, and yet more preferably not more than 20 mass %. Specifically, the concentration of the organic hydrophobic antimicrobial agent in the antimicrobial agent solution is preferably between 0.5 mass % and 50 mass % inclusive, more preferably between 1 mass % and 35 mass % inclusive, even more preferably between 3 mass % and 25 mass % inclusive, and yet more preferably between 5 mass % and 20 mass % inclusive. It is possible to cause the organic hydrophobic antimicrobial agent to uniformly adhere to the absorbent resin by using an antimicrobial agent solution having a concentration within an above-described range.

When mixing the antimicrobial agent solution with the absorbent resin, the ratio of the antimicrobial agent solution to the absorbent resin is preferably a ratio at which the mass of the organic hydrophobic antimicrobial agent in the antimicrobial agent solution relative to the mass of the absorbent resin is not less than 0.001 mass %, more preferably not less than 0.005 mass %, even more preferably not less than 0.01 mass %, and yet more preferably not less than 0.05 mass %. Also, the above-described ratio is preferably a ratio at which the ratio of the mass of the organic hydrophobic antimicrobial agent in the antimicrobial agent solution relative to the mass of the absorbent resin is not more than 1 mass %, more preferably not more than 0.7 mass %, and even more preferably not more than 0.5 mass %. Specifically, the above-described ratio is preferably a ratio at which the ratio of the mass of the organic hydrophobic antimicrobial agent in the antimicrobial agent solution relative to the mass of the absorbent resin is between 0.001 mass % and 1 mass % inclusive, more preferably between 0.005 mass % and 0.7 mass % inclusive, even more preferably between 0.01 mass % and 0.5 mass % inclusive, and yet more preferably between 0.05 mass % and 0.5 mass % inclusive. It is possible to cause the organic hydrophobic antimicrobial agent to uniformly adhere to absorbent resin by mixing the antimicrobial agent solution with the absorbent resin at a ratio within an above-described range. Moreover, even when the organic solvent is left to remain after the antimicrobial agent solution has been mixed with the absorbent resin, the absorbent resin composition can have favorable ease of handling, in particular, flowability.

Moreover, when mixing the antimicrobial agent solution with the absorbent resin, the ratio of the antimicrobial agent solution to the absorbent resin is preferably a ratio at which the mass of the organic solvent in the antimicrobial agent solution relative to the mass of the absorbent resin is not less than 0.01 mass %, more preferably not less than 0.02 mass %, even more preferably not less than 0.03 mass %, and yet more preferably not less than 0.05 mass %. Also, the above-described ratio is preferably a ratio at which the mass of the organic solvent in the antimicrobial agent solution relative to the mass of the absorbent resin is not more than 10 mass %, more preferably not more than 7 mass %, even more preferably not more than 5 mass %, and yet more preferably not more than 3 mass %. Specifically, the above-described ratio is preferably a ratio at which the mass of the organic solvent in the antimicrobial agent solution relative to the mass of the absorbent resin is between 0.01 mass % and 10 mass % inclusive, more preferably between 0.02 mass % and 7 mass % inclusive, even more preferably between 0.03 mass % and 5 mass % inclusive, and yet more preferably between 0.05 mass % and 3 mass % inclusive. It is possible to cause the organic hydrophobic antimicrobial agent to uniformly adhere to the absorbent resin by mixing the antimicrobial agent solution with the absorbent resin at a ratio within an above-described range. Moreover, even when the organic solvent is left to remain after the antimicrobial agent solution has been mixed with the absorbent resin, the absorbent resin composition can have favorable ease of handling, in particular, flowability.

When mixing the antimicrobial agent solution with the absorbent resin, the antimicrobial agent solution may be added to the absorbent resin, or conversely, the absorbent resin may be added to the antimicrobial agent solution. Alternatively, the antimicrobial agent solution and the absorbent resin may be added at the same time.

After the antimicrobial agent solution has been mixed with the absorbent resin, the organic solvent may be removed through heating, pressure reduction, or other means as necessary. It goes without saying that the organic solvent may also be left to remain without being removed. In either case, a step of mixing the mixed absorbent resin with inorganic fine particles may further be performed as a downstream step. It is possible to provide the inorganic fine particles to the absorbent resin by performing this step. Providing the inorganic fine particles to the absorbent resin is advantageous in improving the powder characteristics, in particular, the flowability of the absorbent resin composition to be obtained.

Examples of the inorganic fine particles include silica fine particles, zirconia oxide, aluminum oxide, iron oxide, zinc oxide, and gold, and these types of inorganic fine particles can be used alone or in combination of two or more. Among these inorganic fine particles, silica fine particles are especially preferably used.

A synthetic amorphous silica is preferably used for the silica fine particles. Synthetic amorphous silicas are broadly divided into those manufactured by using a dry method and those manufactured by using a wet method: the former synthetic amorphous silicas include dry silica, and the latter synthetic amorphous silicas include wet silica, silica gel, and colloidal silica. From the standpoint of causing silica to uniformly adhere to the absorbent resin, dry silica is especially preferable. For example, dry silica marketed by Nippon Aerosil Co., Ltd under the trade name AEROSIL can be preferably used as the dry silica.

In terms of ease of handling and adhesion to the absorbent resin, the average primary particle size of the inorganic fine particles is preferably not less than 5 nm and more preferably not less than 10 nm, and also preferably not more than 500 nm and more preferably not more than 100 nm. More specifically, the average primary particle size of the inorganic fine particles is preferably between 5 nm and 500 nm inclusive and more preferably between 10 nm and 100 nm inclusive. The average primary particle size of the inorganic fine particles refers to an arithmetic mean value of the Feret diameter that is measured by observing not less than 100 particles under a transmission electron microscope.

When mixing the inorganic fine particles with the absorbent resin that has been mixed with the antimicrobial agent solution, the ratio of the inorganic fine particles to the absorbent resin is preferably a ratio at which the mass of the inorganic fine particles relative to the mass of the fed absorbent resin, that is, the absorbent resin before being mixed with the antimicrobial agent solution is not less than 0.01 mass %, more preferably not less than 0.05 mass %, even more preferably not less than 0.1 mass %, and yet more preferably not less than 0.2 mass %. Also, the mass of the inorganic fine particles relative to the mass of the absorbent resin that has been fed is preferably not more than 5 mass %, more preferably not more than 4 mass %, even more preferably not more than 3 mass %, and yet more preferably not more than 2 mass %. Specifically, the mass of the inorganic fine particles relative to the mass of the absorbent resin that has been fed is preferably between 0.01 mass % and 5 mass % inclusive, more preferably between 0.05 mass % and 4 mass % inclusive, even more preferably between 0.1 mass % and 3 mass % inclusive, and yet more preferably between 0.2 mass % and 2 mass % inclusive. It is possible to cause the inorganic fine particles to uniformly adhere to the absorbent resin by mixing the inorganic fine particles with the absorbent resin at a ratio within an above-described range, and thus it is possible to improve the powder characteristics, in particular, the flowability of the absorbent resin composition to be obtained.

After the antimicrobial agent solution has been mixed with the absorbent resin, when mixing the absorbent resin with the inorganic fine particles, the inorganic fine particles may be added to the absorbent resin that has been mixed with the antimicrobial agent solution, or conversely, the absorbent resin that has been mixed with the antimicrobial agent solution may be added to the inorganic fine particles. Alternatively, the inorganic fine particles and the absorbent resin that has been mixed with the antimicrobial agent solution may be mixed at the same time.

Moreover, an additive may also be dissolved or dispersed in the solution in which the antimicrobial agent is dissolved in the organic solvent. Preferably, the additive is a perfume.

The foregoing description relates to the step of mixing the antimicrobial agent solution with the absorbent resin and then mixing the absorbent resin with the inorganic fine particles. However, instead of this step, it is also possible to mix the absorbent resin with the inorganic fine particles to cause the inorganic fine particles to adhere to the absorbent resin, and then mix the absorbent resin to which the inorganic fine particles adhere with the antimicrobial agent solution.

With the above-described method, an absorbent resin composition in a state in which at least an antimicrobial agent adheres to the surface of the absorbent resin can be obtained, and in certain cases, an absorbent resin composition in which an antimicrobial agent and an organic solvent adhere to the absorbent resin can be obtained. In this absorbent resin composition, due to the hydrophobicity of the antimicrobial agent, at least the antimicrobial agent discontinuously adheres to the surface of the absorbent resin, and in certain cases, the antimicrobial agent and the organic solvent discontinuously adhere to the surface of the absorbent resin. In other words, if the surface of the absorbent resin is compared to a sea, at least the antimicrobial agent is present in a state in which it is scattered like islands in the sea, and in certain cases, the antimicrobial agent and the organic solvent are present in a state in which they are scattered like islands in the sea. Since at least the antimicrobial agent covers the surface of the absorbent resin in the above-described state, the flowability of the absorbent resin composition is improved even more. From the standpoint of achieving an even more remarkable effect of improving flowability, the coverage of the surface of the absorbent resin by the antimicrobial agent is preferably not less than 5%, more preferably not less than 7%, and even more preferably not less than 15%. Also, the coverage by the antimicrobial agent is preferably not more than 40%, more preferably not more than 30%, and even more preferably not more than 25%. The coverage by the antimicrobial agent is preferably between 5% and 40% inclusive, more preferably between 7% and 30% inclusive, and even more preferably between 15% and 25% inclusive.

The coverage of the surface of the absorbent resin by the antimicrobial agent can be measured through electron spectroscopy for chemical analysis (ESCA). A specific method of measurement is as follows. The adhesive force of an adhesive that joins constituent members of an absorbent article is weakened by using a cold spray, and an absorbent member is removed by carefully peeling off the constituent members. The absorbent resin is roughly removed from the absorbent member by using a sieve having a mesh size of 1 mm to 5 mm. Furthermore, the pulp and the absorbent resin are separated through vibration, and only the absorbent resin is removed. The absorbent resin is uniformly fixed to a sample platform with a double-faced carbon tape and without leaving a space. At this time, the absorbent resin is fixed such that the surface of the absorbent resin is flat. A PHI Quantera SXM (ULVAC-PHI Inc.) measurement device is used. The measurement conditions are as follows: X-ray source: monochromatic AlKα radiation 1486.6 eV, 25 W, 15 kV; and with respect to a beam system, 500 μm×500 μm; Pass energy: 280.0 eV (survey), 112.0 eV (narrow); Step: 1.00 eV (survey), 0.20 eV (narrow); charge correction: Newtralizer and Ar$^+$ irradiation; photoelectron take-off angle: 45 degrees; elements to be detected: C1s (15), N1s (50), O1s (10), Na1s (15), and Si2p (20); and correction of the binding energy position is performed with C1s284.8 cV derived from CH of carbon. The coverage is calculated by using an equation below.

Coverage by antimicrobial agent=amount of decrease in surface element concentration of "Na" after treatment with antimicrobial agent/surface element concentration of "Na" before treatment (matrix absorbent resin)

In the case where the material for an absorbent article of the present invention is an absorbent resin composition, the yield of the fed organic hydrophobic antimicrobial agent is preferably not less than 70 mass %, more preferably not less than 80 mass %, even more preferably not less than 90 mass %, and yet more preferably not less than 95 mass %. In relation to this, in the case where the material for an absorbent article of the present invention is the absorbent resin composition, the proportion of the organic hydrophobic antimicrobial agent in the absorbent resin composition is preferably not less than 0.005 mass %, more preferably not less than 0.01 mass %, and even more preferably not less than 0.05 mass %. Also, the proportion of the organic hydrophobic antimicrobial agent is preferably not more than 5.0 mass %, more preferably not more than 1.0 mass %, and even more preferably not more than 0.5 mass %. The proportion of the organic hydrophobic antimicrobial agent in the absorbent resin composition is preferably between 0.005 mass % and 5.0 mass % inclusive, more preferably between 0.01 mass % and 1.0 mass % inclusive, and even more preferably between 0.05 mass % and 0.05 mass % inclusive.

Moreover, in the case where an absorbent resin composition in which the organic solvent still remains is obtained without removing the organic solvent, the yield of the organic solvent is preferably not less than 70 mass %, more preferably not less than 80 mass %, even more preferably not less than 90 mass %, and yet more preferably not less than 95 mass %. In relation to this, in the absorbent resin composition of the present invention, the proportion of the organic solvent in the absorbent resin composition is preferably not less than 0.1 mass %, more preferably not less than 0.5 mass %, and even more preferably not less than 1.0 mass %. Also, the proportion of the organic solvent is preferably not more than 7.0 mass %, more preferably not more than 5.0 mass %, and even more preferably not more than 3.5 mass %. The proportion of the organic solvent in the absorbent resin composition is preferably between 0.1 mass % and 7.0 mass % inclusive, more preferably between 0.5 mass % and 5.0 mass % inclusive, and even more preferably between 1.0 mass % and 3.5 mass % inclusive.

In the case where the inorganic fine particles are caused to adhere to the absorbent resin, the proportion of the inorganic fine particles in the absorbent resin composition is preferably not less than 0.01 mass %, more preferably not less than 0.05 mass %, and even more preferably not less than 0.1 mass %. Moreover, the proportion of the inorganic fine particles is preferably not less than 5.0 mass %, more preferably not less than 3.0 mass %, and even more preferably not less than 1.0 mass %. The proportion of the inorganic fine particles in the absorbent resin composition is preferably between 0.01 mass % and 5.0 mass % inclusive, more preferably between 0.05 mass % and 3.0 mass % inclusive, and even more preferably between 0.1 mass % and 1.0 mass % inclusive.

The proportions of the organic hydrophobic antimicrobial agent, the organic solvent, and the inorganic fine particles contained in the absorbent resin composition are individually measured by using the following methods. That is to say, the proportions of the organic hydrophobic antimicrobial agent and the organic solvent are measured by performing extraction with a solvent such as ethanol and methanol and performing measurement by using a convenient method of measurement, such as liquid chromatography, in accordance with the structure of each agent. The proportion of inorganic fine particles is measured using the absorbent resin as is, and the measurement is performed by quantitatively analyzing the atomic weight of the metals of the absorbent resin composition through energy dispersive X-ray spectroscopy (EDX) or electron spectroscopy for chemical analysis (ESCA).

According to the present invention, the absorbent resin composition having a powder-like external appearance can be easily manufactured. Moreover, the absorbent resin composition having favorable powder flowability can be manufactured. Typical examples of characteristic values related to the powder flowability are the angle of repose and the angle of spatula. The angle of repose of the absorbent resin composition that is obtained according to the present invention is preferably not less than 30 degrees, more preferably not less than 32 degrees, and even more preferably not less than 34 degrees. Also, the angle of repose is preferably not more than 45 degrees, more preferably not more than 43 degrees, even more preferably not more than 41 degrees, and yet more preferably not more than 39 degrees. Specifically, the angle of repose is preferably between 30 degrees and 45 degrees inclusive, more preferably between 32 degrees and 43 degrees inclusive, even more preferably between 34 degrees and 41 degrees inclusive, and yet more preferably between 34 degrees and 39 degrees inclusive. The angle of repose can be measured by using a Powder Tester PT-R manufactured by Hosokawa Micron Corporation.

On the other hand, the angle of spatula is preferably not less than 40 degrees, more preferably not less than 41 degrees, even more preferably not less than 42 degrees, and yet more preferably not less than 43 degrees. Also, the angle of spatula is preferably not more than 60 degrees, more preferably not more than 58 degrees, even more preferably not more than 56 degrees, and yet more preferably not more than 54 degrees. Specifically, the angle of repose is preferably between 40 degrees and 60 degrees inclusive, more preferably between 41 degrees and 58 degrees inclusive, even more preferably between 42 degrees and 56 degrees inclusive, and yet more preferably between 43 and 54 degrees inclusive. The angle of spatula can be measured by using a Powder Tester PT-R manufactured by Hosokawa Micron Corporation. An average of the values that are respectively measured before applying a shock and after applying a shock once is used as the angle of spatula.

In the case where the material for an absorbent article of the present invention is the absorbent resin composition, another example of the characteristics values related to the flowability of the absorbent resin composition is the angle of fall. The angle of fall of the absorbent resin composition is preferably not less than 30 degrees, more preferably not less than 31 degrees, even more preferably not less than 32 degrees, and yet more preferably not less than 33 degrees. Also, the angle of fall is preferably not more than 42 degrees, more preferably not more than 41 degrees, even more preferably not more than 40 degrees, and yet more preferably not more than 39 degrees. Specifically, the angle of fall is preferably between 30 degrees and 42 degrees inclusive, more preferably between 31 degrees and 41 degrees inclusive, even more preferably between 32 degrees and 40 degrees inclusive, and yet more preferably between 33 degrees and 39 degrees inclusive. The angle of fall can be measured by using a Powder Tester PT-R manufactured by Hosokawa Micron Corporation. A value that is measured after a shock has been applied three times is used as the angle of fall.

In the case where the material for an absorbent article of the present invention is the absorbent resin composition, examples of the other powder characteristics of the absorbent resin composition include the loose apparent specific gravity and the compressibility. The loose apparent specific gravity of the absorbent resin composition is preferably not less than 0.55 g/mL, more preferably not less than 0.60 g/mL, and even more preferably not less than 0.62 g/mL. Also, the loose apparent specific gravity is preferably not more than 0.80 g/mL, more preferably not more than 0.79 g/mL, and even more preferably not more than 0.78 g/mL. Specifically, the loose apparent specific gravity is preferably between 0.55 g/mL and 0.80 g/mL inclusive, more preferably between 0.60 g/mL and 0.79 g/mL inclusive, and even more preferably between 0.62 g/mL and 0.78 g/mL inclusive.

On the other hand, the compressibility is a value defined by [(packed apparent specific gravity−loose apparent specific gravity)/packed apparent specific gravity]×100. The compressibility of the absorbent resin composition is preferably not less than 4%, more preferably not less than 5%, and even more preferably not less than 6%. Also, the compressibility is preferably not more than 15%, more preferably not more than 14%, and even more preferably not more than 13%. Specifically, the compressibility is preferably between 4% and 15% inclusive, more preferably between 5% and 14% inclusive, and even more preferably between 6% and 13% inclusive.

The loose apparent specific gravity and the packed apparent specific gravity are measurement values of the powder characteristics for obtaining the compressibility of powder. The loose apparent specific gravity is a measurement value that is derived by filling a cup having a given capacity with powder by allowing the powder to free fall into the cup, and then weighing the powder, and indicates a packing density in a state in which the powder has been allowed to free fall. The packed apparent specific gravity is an apparent specific gravity in a state in which the filled specimen with which the loose apparent specific gravity has been measured is deaerated by being tapped and thus most densely packed. These specific gravities can be measured in conformity with ASTM standards, and a powder characteristics evaluation device PT-R (Hosokawa Micron Corporation) or the like can be used as the measuring device.

As described above, according to the present invention, the absorbent resin composition having favorable powder flowability can be obtained, and thus, the absorbent resin composition can be pneumatically conveyed easily. For example, as shown in FIG. 1, in a fiber stacking apparatus 10 for manufacturing an absorbent member of an absorbent article, the absorbent resin composition (not shown) stored in a storage tank 11 can be pneumatically conveyed into a hood 13 of the fiber stacking apparatus 10 via a supply duct 12. Moreover, the absorbent resin composition (not shown) supplied into the hood 13 can be entrained in a conveyance airflow flowing through the hood 13 and supplied onto a circumferential surface of a fiber stacking drum 14.

The absorbent resin composition is preferably used for an absorbent article. The absorbent article is an article that is preferably used to absorb a liquid discharged from the body. Having the absorbent resin composition of the present invention, the absorbent article has high antimicrobial performance and is thus unlikely to cause inconvenience, such as unpleasant odors and skin irritation, attributable to excreta, and the absorbent article also has excellent absorption performance for excreta such as urine and is thus unlikely to allow excreta to leak.

Examples of the form in which the absorbent resin composition is contained in the absorbent article include (1) a form in which absorbent resin composition particles are spread between layers of fibrous materials, such as pulp and thermal-fusion-bondable fibers, that are arranged in layers; (2) a form in which the absorbent resin composition is mixed with fibrous materials, such as pulp and thermal-fusion-bondable fibers; and (3) a form in which the absorbent resin composition is sandwiched between two or more water-absorbing sheets or nonwoven fabrics. The content of the absorbent resin composition in the absorbent article can be appropriately determined in accordance with the type and size of the absorbent article and the absorption performance to be attained.

The absorbent article having the absorbent resin composition of the present invention typically includes a liquid permeable topsheet that can come into contact with the skin of a wearer when the absorbent article is worn, a liquid impermeable or water repellent backsheet, and a liquid-retentive absorbent member disposed between the two sheets. Various types of nonwoven fabrics or porous synthetic resin sheets or the like can be used as the topsheet. A synthetic resin film made from polyethylene, polypropylene, polyvinyl chloride, or the like, a composite material of a synthetic resin film and a nonwoven fabric, or the like can be used as the backsheet. The absorbent article may further include various members adapted for specific uses of the absorbent article. Such members are known to those skilled in the art. For example, in the case where the absorbent article is applied to a disposable diaper or a sanitary napkin, one or two or more pairs of leak-proof cuffs can be disposed on both lateral side portions of the topsheet.

For example, an absorbent core in which an absorbent resin composition that is manufactured by using the present manufacturing method is retained by a fiber aggregate including a fiber material such as pulp fibers can be used as the absorbent member of the absorbent article. The absorbent core may also be covered by a water permeable cover sheet made of tissue paper, a nonwoven fabric, or the like. Another example of the absorbent member is an absorbent member having an absorbent sheet containing the absorbent resin composition that is obtained by using the present manufacturing method. The absorbent member in this case has, for example, a structure in which a single absorbent sheet is folded or a structure in which a plurality of absorbent sheets are laminated. For example, an absorbent sheet can be used as the absorbent sheet, the absorbent sheet being made into a sheet-like shape by bonding constituent fibers to each other or constituent fibers to the absorbent resin composition via an adhesive force that is generated in the absorbent resin composition in a wet state and a separately added binder such as an adhesive or adhesive fibers. Favorable absorbent sheets include an absorbent sheet in which the absorbent resin composition is fixed to an aggregate of pulp fibers, a dry pulp sheet manufactured by using an air-laying method, and an absorbent sheet in which the absorbent resin composition in a particulate form is spread between two nonwoven fabrics.

The absorbent article of the present invention broadly embraces articles that are used to absorb bodily fluids, such as urine, menstrual blood, loose stools, and sweat, for example, discharged from the human body, and disposable diapers, sanitary napkins, sanitary shorts, and the like are embraced therein.

Next, another embodiment of the material for an absorbent article of the present invention will be described. The material for an absorbent article of the present invention may be a sheet material. That is to say, the material for an absorbent article of the present invention may be a sheet for an absorbent article. In this case, a specific application example of the sheet for an absorbent article is a cover sheet that covers at least a skin-facing surface side of the absorbent core. This cover sheet is also called a core wrap sheet. Examples of the absorbent core covered by the cover sheet include a mixed fiber stack of fluff pulp and a water-absorbent polymer, a deposit composed of only an absorbent polymer, and a fiber stack composed of only fluff pulp. The absorbent member is configured by covering at least the skin-facing surface side of the absorbent core with the cover sheet. The topsheet is disposed on a skin-facing surface side of the cover sheet. Other application examples of the sheet for an absorbent article include scrub suits, bandages, adhesive bandages, bed sheets, pillow cases, absorbent paper for armpit pads, and antimicrobial paper for shoes that are used for medical purposes, industrial materials, everyday materials, and the like and that are particularly required to have antimicrobial performance.

It is preferable that the sheet for an absorbent article has a configuration in which the antimicrobial agent and the organic solvent are contained in a substrate sheet. As the antimicrobial agent, one antimicrobial agent can be used alone, or a combination of two or more antimicrobial agents can be used. Similarly, as the organic solvent, one organic solvent can be used alone, or a combination of two or more organic solvents can be used. The sheet for an absorbent article may also contain water, and in terms of the antimicrobial performance, the water content is preferably not more than 10 mass % with respect to the mass of the sheet for an absorbent article. A water content of not more than 10 mass % is approximately equal to the amount of water that is inevitably naturally absorbed from an ambient environment by the sheet for an absorbent article when placed in the ambient environment. The amount of water contained in the sheet for an absorbent article is measured in conformity with the Paper and board—Determination of moisture content of a lot—Oven drying method (105° C.±2° C., drying time: 30 minutes or more) specified in the Japanese Industrial Standards JISP8127.

It is preferable that the sheet for an absorbent article has liquid permeability. From this point of view, it is preferable that the substrate sheet constituting a sheet for an absorbent article is a fiber sheet or a perforated sheet in which a plurality of through-holes are formed in a film. Examples of the fiber sheet include paper, nonwoven fabrics, woven fabrics, woven textiles, and composite materials thereof. The basis weight of the substrate sheet constituting the sheet for an absorbent article is preferably not less than 50 g/m$^2$, more preferably not less than 70 g/m$^2$, and even more preferably not less than 100 g/m$^2$. Also, the basis weight of the substrate sheet is preferably not more than 1000 g/m$^2$, more preferably not more than 500 g/m$^2$, and even more preferably not more than 300 g/m$^2$. The basis weight of the sheet for an absorbent article is preferably between 10 g/m$^2$ and 50 g/m$^2$ inclusive, more preferably between 12 g/m$^2$ and 40 g/m$^2$ inclusive, and even more preferably between 13 g/m$^2$ and 35 g/m$^2$ inclusive.

It is preferable that the sheet for an absorbent article is configured by applying an antimicrobial agent solution containing the antimicrobial agent and the organic solvent to the substrate sheet. The antimicrobial agent solution may also contain water. In terms of the stability of the antimicrobial agent solution and suppression of foaming and precipitation of the antimicrobial agent in the antimicrobial agent solution, it is preferable that the water content is not more than 8 mass % with respect to the mass of the antimicrobial agent solution. A water content of not more than 8 mass % is approximately equal to the amount of water that is inevitably naturally absorbed from an ambient environment by the antimicrobial agent solution when placed in the ambient environment. Methods of analyses including the qualitative analysis for determining whether or not the sheet for an absorbent article contains the antimicrobial agent and the quantitative analysis that is to be performed in the case where the sheet for an absorbent article contains the antimicrobial agent are as follows.

Methods of analyses: Various materials of a commercially available product are carefully peeled off by weakening the adhesive force of an adhesive by using a cold spray or the like. The materials are first subjected to fluorescent X-ray diffraction to check whether or not the materials contain any metal. With respect to agents (antimicrobial agent and organic solvent) other than metals, each material is immersed in a methanol solution, and then, the agents contained in the methanol solution are fractionated by using an HPLC or the like. Compounds contained in the fractions are identified by using an NMR measuring device or the like. Quantification is performed by calculating the concentrations of the agents in the methanol solution by using LC-UV or the like.

Moreover, the sheet for an absorbent article of the present invention may also be configured by applying an antimicrobial agent solution containing water in an amount of not more than 30 mass % to the substrate sheet. In this case, a step of removing water through drying is provided after the application of the antimicrobial agent solution to the substrate sheet. Well-known methods such as a method in which hot air is applied to the substrate sheet, a method in which the substrate sheet is run along a heated roller, and the like can be used, without limitation, as drying means.

The antimicrobial agent and the organic solvent may be uniformly present over the entire region of the sheet for an absorbent article. Alternatively, the antimicrobial agent and the organic solvent may be present locally in a specific portion of the sheet for an absorbent article. In either case, the amount of antimicrobial agent that is present in the sheet for an absorbent article is preferably not less than 0.02 g/m$^2$, more preferably not less than 0.04 g/m$^2$, and even more preferably not less than 0.05 g/m$^2$. Also, the amount of antimicrobial agent that is present in the sheet for an absorbent article is preferably not more than 0.5 g/m$^2$, more preferably not more than 0.4 g/m$^2$, and even more preferably not more than 0.3 g/m$^2$. The amount of antimicrobial agent that is present in the sheet for an absorbent article is preferably between 0.02 g/m$^2$ and 0.5 g/m$^2$ inclusive, and more preferably between 0.04 g/m$^2$ and 0.4 g/m$^2$ inclusive, and even more preferably between 0.05 g/m$^2$ and 0.3 g/m$^2$ inclusive. The amount of antimicrobial agent that is present in the sheet for an absorbent article is calculated based on the total area the sheet for an absorbent article even in the case where the antimicrobial agent is present locally.

The amount of organic solvent that is present in the sheet for an absorbent article is preferably not less than 0.1 g/m$^2$, more preferably not less than 0.2 g/m$^2$, and even more preferably not less than 0.4 g/m$^2$. Also, the amount of organic solvent that is present in the sheet for an absorbent article is preferably not more than 20 g/m$^2$, more preferably not more than 15 g/m$^2$, and even more preferably not more than 12 g/m$^2$. The amount of organic solvent that is present in the sheet for an absorbent article is preferably between 0.1 g/m$^2$ and 20 g/m$^2$ inclusive, more preferably between 0.2 g/m$^2$ and 15 g/m$^2$ inclusive, and even more preferably between 0.4 g/m$^2$ and 12 g/m$^2$ inclusive. The amount of organic solvent that is present in the sheet for an absorbent article is calculated based on the total area of the sheet for an absorbent article even in the case where the organic solvent is present locally.

With regard to the ratio between the used amount of the antimicrobial agent and the used amount of the organic solvent, the mass of the organic solvent is preferably not less than 4 times, more preferably not less than 5 times, and even more preferably not less than 8 times the mass of the antimicrobial agent. Also, the mass of the organic solvent is preferably not more than 1000 times, more preferably not more than 100 times, and even more preferably not more than 50 times the mass of the antimicrobial agent. The mass of the organic solvent is preferably between 4 times and 1000 times, inclusive, more preferably between 5 times and 100 times, inclusive, and even more preferably between 8 times and 50 times, inclusive, the mass of the antimicrobial agent. Setting the ratio between the used amount of the antimicrobial agent and the used amount of the organic solvent within an above-described range is preferable in that the solubility of the antimicrobial agent and the ease of application of the antimicrobial agent solution are favorable, and the ease of uniform application during spraying or spreading is improved.

In the present invention, instead of or in addition to the configuration in which the sheet for an absorbent article contains the antimicrobial agent and the organic solvent, an embodiment can also be adapted in which the absorbent core contains the antimicrobial agent and the organic solvent. In the case of this embodiment, the amount of antimicrobial agent that is present in the absorbent core is preferably not less than 0.01 g/m$^2$, more preferably not less than 0.05 g/m$^2$, and even more preferably not less than 0.1 g/m$^2$. Also, the amount of antimicrobial agent that is present in the absorbent core is preferably not more than 10.0 g/m$^2$, more preferably not more than 5.0 g/m$^2$, and even more preferably not more than 2.0 g/m$^2$. The amount of antimicrobial agent that is present in the absorbent core is preferably between 0.01 g/m$^2$ and 10.0 g/m$^2$ inclusive, more preferably between 0.05 g/m$^2$ and 5.0 g/m$^2$ inclusive, and even more preferably between 0.1 g/m$^2$ and 2.0 g/m$^2$ inclusive. The amount of antimicrobial agent that is present in the absorbent core is calculated based on the total area of the absorbent core even in the case where the antimicrobial agent is present locally.

On the other hand, the amount of organic solvent that is present in the absorbent core is preferably not less than 0.01 g/m$^2$, more preferably not less than 0.02 g/m$^2$, and even more preferably not less than 0.05 g/m$^2$. Also, the amount of organic solvent that is present in the absorbent core is preferably not less than 10 g/m$^2$, more preferably not less than 5 g/m$^2$, and even more preferably not less than 3 g/m$^2$. The amount of organic solvent in the absorbent core is preferably between 0.01 g/m$^2$ and 10 g/m$^2$ inclusive, more preferably between 0.02 g/m² and 5 g/m² inclusive, and even more preferably between 0.05 g/m² and 3 g/m² inclusive. The amount of organic solvent in the absorbent core is calculated based on the total area of the absorbent core even in the case where the organic solvent is present locally.

In the case where the absorbent core contains the antimicrobial agent and the organic solvent, the ratio of the used amount of the antimicrobial agent to the used amount of the organic solvent can be set to the same ratio as the ratio of the antimicrobial agent to the organic solvent in the case where the sheet for an absorbent article contains the antimicrobial agent and the organic solvent.

The absorbent core may also contain water, and the water content is preferably not more than 10 mass % with respect to the mass of the absorbent core. The reason for this is as described above. A water content of not more than 10 mass % is approximately equal to the amount of water that is inevitably naturally absorbed from an ambient environment by the absorbent core when placed in the ambient environment. The amount of water contained in the absorbent core is measured by using the same method as the above-described method for measuring the amount of water contained in the sheet for an absorbent article.

Regardless of whether the antimicrobial agent is contained in the sheet for an absorbent article or the absorbent core, it is preferable that an organic hydrophobic antimicrobial agent is used as the antimicrobial agent. The reason for this is as described above. Preferably, any of the above-described organic compounds represented by formula (1) or (2) is used as the organic hydrophobic antimicrobial agent. The reason for this is that these organic compounds have a high antimicrobial effect and low skin irritancy. These organic compounds can be used alone or in combination of two or more.

In order to cause the organic hydrophobic antimicrobial agent to adhere to the substrate sheet and/or the absorbent core, in the present invention, it is preferable to adopt a step of forming an antimicrobial agent by dissolving the organic hydrophobic antimicrobial agent in the organic solvent, and making the substrate sheet and/or the absorbent core contain the antimicrobial agent solution. Preferably, the antimicrobial agent solution is a solution in which the organic hydrophobic antimicrobial agent is completely dissolved. In the case where an undissolved portion of the organic hydrophobic antimicrobial agent is present in the antimicrobial agent solution, if the substrate sheet and/or the absorbent core is made to contain such an antimicrobial agent solution, there is a possibility that the organic hydrophobic antimicrobial agent may non-uniformly adhere to the substrate sheet and/or the absorbent core.

It is preferable that the organic solvent contained in the antimicrobial agent solution is a liquid at 25° C. An organic solvent in which the organic hydrophobic antimicrobial agent can be dissolved is used as the organic solvent. Specific examples of such an organic solvent are as described above.

It is preferable that the organic solvent has low volatility. The reason for this is as described above. With the use of an organic solvent having low volatility, after the substrate sheet and/or the absorbent core has been made to contain the antimicrobial agent solution, the organic solvent can be left to remain in the sheet for an absorbent article and/or the absorbent article (in the absorbent core).

From the above-described point of view, it is preferable that the vapor pressure of the organic solvent at 25° C. is not more than 30 Pa. An organic solvent having a vapor pressure at 25° C. of not more than 30 Pa is referred to as "non-volatile organic solvent" in the present invention. In particular, the vapor pressure of the organic solvent at 25° C. is more preferably not more than 20 Pa, even more preferably not more than 15 Pa, and yet more preferably not more than 10 Pa.

It is particularly preferable that the organic solvent has the above-described non-volatility in addition to having the above-described hydrophilicity.

The concentration of the organic hydrophobic antimicrobial agent in the antimicrobial agent solution is preferably not less than 0.5 mass %, more preferably not less than 1 mass %, even more preferably not less than 3 mass %, and yet more preferably not less than 5 mass %. Also, the concentration of the organic hydrophobic antimicrobial agent in the antimicrobial agent solution is preferably not more than 50 mass %, more preferably not more than 35 mass %, even more preferably not more than 25 mass %, and yet more preferably not more than 20 mass %. Specifically, the concentration of the organic hydrophobic antimicrobial agent in the antimicrobial agent solution is preferably between 0.5 mass % and 50 mass % inclusive, more preferably between 1 mass % and 35 mass % inclusive, even more preferably between 3 mass % and 25 mass % inclusive, and yet more preferably between 5 mass % and 20 mass % inclusive. It is possible to cause the organic hydrophobic antimicrobial agent to uniformly adhere to the substrate sheet and/or the absorbent core by using the antimicrobial agent solution at a concentration within an above-described range. It should be noted that although water is allowed to be contained in the antimicrobial agent solution as described above, the water content is preferably not more than 8 mass %.

It is preferable that, when the antimicrobial agent solution is applied to the substrate sheet and/or the absorbent core, the ratio of the antimicrobial agent solution to the substrate sheet and/or the absorbent core is set such that, based on the total area of the sheet for an absorbent article and/or the absorbent core to be obtained, the basis weights of the organic hydrophobic antimicrobial agent and the organic solvent contained in the antimicrobial agent solution are respectively within an above-described range. It is possible to cause the organic hydrophobic antimicrobial agent to uniformly adhere to the substrate sheet and/or the absorbent core by mixing the antimicrobial agent solution with the substrate sheet and/or the absorbent core at a ratio that is set as described above. Moreover, even when the organic solvent in the antimicrobial agent solution is left to remain in the sheet for an absorbent article and/or the absorbent core after the antimicrobial agent solution has been mixed with the substrate sheet and/or the absorbent core, the sheet for an absorbent article and/or the absorbent core to be obtained can have favorable ease of handling, in particular, flowability.

With regard to the method for applying the antimicrobial agent solution to the substrate sheet and/or the absorbent core, dripping can be used in the case where the antimicrobial agent solution is applied partially, for example. Spraying can be used in the case where the antimicrobial agent solution is to be applied over the entire surface. In addition, various printing methods, a method in which the substrate sheet and/or the absorbent core is immersed in the antimicrobial agent solution, and the like can also be used.

After the antimicrobial agent solution has been applied to the substrate sheet and/or the absorbent core, the organic solvent may be removed through heating, pressure reduction, or other means as necessary. It goes without saying that the organic solvent may also be left to remain without being removed. Not removing the organic solvent is advantageous considering that manufacturing of a member to be obtained can be performed at a basic facility.

A sheet for an absorbent article, and an absorbent core that are to be obtained can be obtained in accordance with the above-described procedures. In the sheet for an absorbent article, and the absorbent core that are thus obtained, even in the state in which the antimicrobial agent solution is applied partially, if these members come into contact with a bodily fluid such as urine, the antimicrobial agent solution is diffused in these members together with the bodily fluid, and thus, a high antimicrobial effect is exhibited over the entire region of these members. In particular, in the case where the sheet for an absorbent article is used as the core wrap sheet that covers the absorbent core, if the core wrap sheet comes into contact with a bodily fluid, the antimicrobial agent solution is diffused in the core wrap sheet together with the bodily fluid and, furthermore, is also diffused in the absorbent core, and thus, a high antimicrobial effect is exhibited over the entire region of the absorbent member. In contrast, even if an antimicrobial agent in a powdery state is provided to these members, it is hard for the antimicrobial agent to be diffused in the members together with the bodily fluid, and therefore, a high antimicrobial effect that is provided by the present invention cannot be obtained.

With regard to the foregoing embodiments, the present invention further discloses a material for an absorbent article, a method for manufacturing the material, and an absorbent article in which the material below is used.

<1>
A material for an absorbent article, the material comprising an organic hydrophobic antimicrobial agent and a hydrophilic non-volatile organic solvent.

<2>
The material for an absorbent article as set forth in clause <1>, wherein the material comprises an absorbent resin composition including the organic hydrophobic antimicrobial agent, the hydrophilic non-volatile organic solvent, and an absorbent resin.

<3>
The material for an absorbent article as set forth in clause <2>, wherein the organic hydrophobic antimicrobial agent and the organic solvent adhere to the absorbent resin in an island-like manner.

<4>
The material for an absorbent article as set forth in clause <3>, wherein the coverage of the surface of the absorbent resin covered by the organic hydrophobic antimicrobial agent is not less than 5%, preferably not less than 7%, and more preferably not less than 15%, and also not more than 40%, preferably not more than 30%, and more preferably not more than 25%.

<5>
The material for an absorbent article as set forth in any one of clauses <2> to <4>, the material further comprising inorganic fine particles.

<6>
The material for an absorbent article as set forth in clause <5>, wherein silica fine particles, zirconia oxide, aluminum oxide, iron oxide, zinc oxide, or gold is used for the inorganic fine particles, and these types of inorganic fine particles are used alone or in combination of two or more.

<7>
The material for an absorbent article as set forth in clause <5> or <6>, wherein the inorganic fine particles have an average primary particle size of preferably not less than 5 nm and more preferably not less than 10 nm, and also preferably not more than 500 nm and more preferably not more than 100 nm.

<8>
The material for an absorbent article as set forth in any one of clauses <2> to <7>, wherein the material has an angle of repose of preferably not less than 30 degrees, more preferably not less than 32 degrees, and even more preferably not less than 34 degrees, and also preferably not more than 45 degrees, more preferably not more than 43 degrees, even more preferably not more than 41 degrees, and yet more preferably not more than 39 degrees.

<9>
The material for an absorbent article as set forth in any one of clauses <2> to <8>, wherein the material has an angle of spatula of preferably not less than 40 degrees, more preferably not less than 41 degrees, even more preferably not less than 42 degrees, and yet more preferably not less than 43 degrees, and also preferably not more than 60 degrees, more preferably not more than 58 degrees, even more preferably not more than 56 degrees, and yet more preferably not more than 54 degrees.

<10>
The material for an absorbent article as set forth in any one of clauses <2> to <9>, wherein the material has an angle of fall of preferably not less than 30 degrees, more preferably not less than 31 degrees, even more preferably not less than 32 degrees, and yet more preferably not less than 33 degrees, and also preferably not more than 42 degrees, more preferably not more than 41 degrees, even more preferably not more than 40 degrees, and yet more preferably not more than 39 degrees.

<11>
The material for an absorbent article as set forth in any one of clauses <2> to <10>, wherein the material has a loose apparent specific gravity of preferably not less than 0.55 g/mL, more preferably not less than 0.60 g/mL, and even more preferably not less than 0.62 g/mL, and also preferably not more than 0.80 g/mL, more preferably not more than 0.79 g/mL, and even more preferably not more than 0.78 g/mL.

<12>
The material for an absorbent article as set forth in clause <1>, wherein the material comprises a sheet for an absorbent article, the sheet containing the organic hydrophobic antimicrobial agent, the hydrophilic non-volatile organic solvent, and water in an amount of not more than 10 mass %.

<13>
The material for an absorbent article as set forth in clause <12>, wherein the sheet for an absorbent article comprises a substrate sheet, the substrate sheet is preferably a fiber sheet or a perforated sheet in which a plurality of through holes are formed in a film, and paper, a nonwoven fabric, a woven fabric, a textile fabric, or a composite material thereof is preferable for the fiber sheet.

<14>
The material for an absorbent article as set forth in clause <1>, the material comprising the organic hydrophobic antimicrobial agent, the hydrophilic non-volatile organic solvent, and an absorbent core.

<15>
The material for an absorbent article as set forth in any one of clauses <1> to <14>, wherein the material contains the organic hydrophobic antimicrobial agent in an amount of not less than 0.02 g/m$^2$, and the organic hydrophobic antimicrobial agent is present in an amount of preferably not less than 0.02 g/m$^2$, more preferably not less than 0.04 g/m², and even more preferably not less than 0.05 g/m², and also preferably not more than 0.5 g/m², more preferably not more than 0.4 g/m², and even more preferably not more than 0.3 g/m².

<16>

The material for an absorbent article as set forth in any one of clauses <1> to <15>, wherein the material contains the organic solvent in a proportion that is between 4 times and 1000 times, inclusive, the mass of the organic hydrophobic antimicrobial agent, and the ratio between the used amount of the antimicrobial agent and the used amount of the organic solvent is such that the mass of the organic solvent is preferably not less than 4 times, more preferably not less than 5 times, and even more preferably not less than 8 times, and also preferably not more than 1000 times, more preferably not more than 100 times, and even more preferably not more than 50 times the mass of the antimicrobial agent.

<17>

The material for an absorbent article as set forth in any one of clauses <1> to <16>, wherein the organic solvent is at least one hydrophilic organic solvent selected from the group consisting of ethylene glycol, propylene glycol, and butylene glycol.

<18>

The material for an absorbent article as set forth in any one of clauses <1> to <17>, wherein the organic hydrophobic antimicrobial agent is an organic compound having a structure represented by formula (1) or (2) below or triclosan:

[Chem. 4]

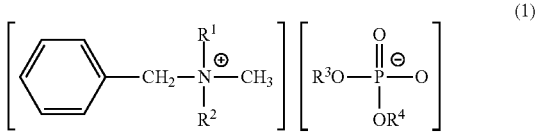

(1)

wherein $R^1$ and $R^2$ each independently represent a methyl group, an ethyl group, a linear or branched alkyl group having 6 to 24 carbon atoms or a linear or branched alkenyl group having 6 to 24 carbon atoms; and one of $R^3$ and $R^4$ represents a linear or branched alkyl group having 6 to 30 carbon atoms, a linear or branched alkenyl group having 6 to 30 carbon atoms or an alkyl-alkylene oxide group (an alkyl moiety and an alkylene moiety in the group may be linear or may be branched), and the other of $R^3$ and $R^4$ represents a hydrogen atom, a methyl group, or an ethyl group, or alternatively, $R^3$ and $R^4$ each independently represent a linear or branched alkyl group having 6 to 30 carbon atom, a linear or branched alkenyl group having 6 to 30 carbon atoms, or an alkyl-alkylene oxide group (an alkyl moiety and an alkylene moiety in the group may be linear or may be branched),

[Chem. 5]

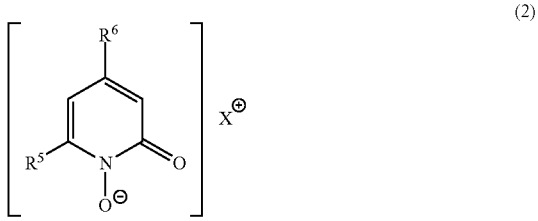

(2)

wherein $R^5$ represents a linear or branched alkyl group having 1 to 30 carbon atoms, a linear or branched alkenyl group having 1 to 30 carbon atoms, an optionally linear or branched cycloalkyl group, an optionally linear or branched aryl group, or an alkyl-alkylene oxide group (an alkyl moiety and an alkylene moiety in the group may be linear or may be branched);

$R^6$ represents a hydrogen atom, a linear or branched alkyl group having 1 to 6 carbon atoms, a linear or branched alkenyl group having 1 to 6 carbon atoms, an optionally linear or branched cycloalkyl group, a phenyl group, or a benzyl group; and $X^+$ represents an alkali metal ion, an alkaline earth metal ion, an ammonium ion, or a divalent to tetravalent cation (excluding an alkaline earth metal ion).

<19>

The material for an absorbent article as set forth in any one of clauses <1> to <18>, wherein the organic hydrophobic antimicrobial agent is benzalkonium cetyl phosphate or piroctone olamine.

<20>

The material for an absorbent article as set forth in any one of clauses <1> to <19>, wherein the organic hydrophobic antimicrobial agent has a solubility in water at 25° C. of preferably not more than 40 g, more preferably not more than 10 g, and even more preferably not more than 1 g.

<21>

The material for an absorbent article as set forth in any one of clauses <1> to <20>, wherein the organic solvent being hydrophilic means that the organic solvent has a solubility of water at 25° C. of not less than 10 mass %.

<22>

The material for an absorbent article as set forth in any one of clauses <1> to <21>, wherein an organic solvent in which the organic hydrophobic antimicrobial agent has a solubility of preferably not less than 5 mass %, more preferably not less than 10 mass %, and even more preferably not less than 15 mass % is used.

<23>

The material for an absorbent article as set forth in any one of clauses <1> to <22>, wherein the organic solvent has a solubility parameter of preferably not less than 12, more preferably not less than 13, even more preferably not less than 13.5, and yet more preferably not less than 14, and also preferably not more than 28, more preferably not more than 27, even more preferably not more than 26, and yet more preferably not more than 25.

<24>

The material for an absorbent article as set forth in any one of clauses <1> to <23>, wherein the organic solvent has a vapor pressure at 25° C. of preferably not more than 30 Pa, more preferably not more than 20 Pa, even more preferably not more than 15 Pa, and yet more preferably not more than 10 Pa.

<25>

The material for an absorbent article as set forth in any one of clauses <1 to <24>, wherein the organic solvent has a flash point of preferably not less than 100° C., more preferably not less than 105° C., even more preferably not less than 110° C., and yet more preferably not less than 115° C.

<26>

The material for an absorbent article as set forth in any one of clauses <1> to <25>, wherein the organic solvent has a viscosity at 25° C. of preferably not less than 5 mPa·s, more preferably not less than 10 mPa·s, even more preferably not less than 30 mPa·s, and yet more preferably not less than 60 mPa·s, and also preferably not more than 1500 mPa·s, more preferably not more than 500 mPa·s, even more preferably not more than 300 mPa·s, and yet more preferably not more than 90 mPa·s.

<27>

The material for an absorbent article as set forth in any one of clauses <1> to <26>, wherein the organic solvent is a water-soluble organic solvent such as a polyhydric alcohol including dihydric alcohols (diols), trihydric alcohols (triols), and tetrahydric or higher polyhydric alcohols.

<28>

The material for an absorbent article as set forth in clause <27>, wherein the alkyl group of the polyhydric alcohol has preferably 2 or more carbon atoms and also preferably 18 or less carbon atoms, more preferably 10 or less carbon atoms, and even more preferably 4 or less carbon atoms.

<29>

The material for an absorbent article as set forth in clause <27> or <28>, wherein the polyhydric alcohol is a lower dihydric alcohol having 2 to 4 carbon atoms,
  the lower dihydric alcohol is at least one hydrophilic organic solvent selected from the group consisting of ethylene glycol, propylene glycol, and butylene glycol,
  the propylene glycol is 1,2-propylene glycol or 1,3-propylene glycol, and
  the butylene glycol is 1,3-butylene glycol, 1,4-butylene glycol, or 2,3-butylene glycol.

<30>

The material for an absorbent article as set forth in any one of clauses <27> to <29>, wherein the organic solvent is at least one hydrophilic organic solvent selected from the group consisting of ethylene glycol, propylene glycol, and butylene glycol.

<31>

The material for an absorbent article as set forth in clause <30>, wherein the propylene glycol is 1,2-propylene glycol or 1,3-propylene glycol, and
  the butylene glycol is 1,3-butylene glycol, 1,4-butylene glycol, or 2,3-butylene glycol.

<32>

An absorbent article comprising the material for an absorbent article as set forth in any one of clauses <1> to <31>.

<33>

An absorbent article comprising:
  an absorbent core;
  a core wrap sheet that is disposed on a skin-facing surface side of the absorbent core; and
  a topsheet that is disposed on a skin-facing surface side of the core wrap sheet,
  wherein the sheet for an absorbent article as set forth in clause <12> is used as the core wrap sheet.

<34>

A method for manufacturing a material for an absorbent article, the method comprising the step of applying an antimicrobial agent solution to a material for an absorbent article, the antimicrobial agent solution being formed by dissolving an organic hydrophobic antimicrobial agent in a hydrophilic non-volatile organic solvent.

<35>

The method for manufacturing a material for an absorbent article as set forth in clause <34>, the method comprising the step of mixing the antimicrobial agent solution with an absorbent resin.

<36>

The method for manufacturing a material for an absorbent article as set forth in clause <35>, the method comprising the step of mixing the absorbent resin with inorganic fine particles prior to or after mixing the antimicrobial agent solution with the absorbent resin.

<37>

The method for manufacturing a material for an absorbent article as set forth in clause <35> or <36>, wherein after the antimicrobial agent solution is mixed with the absorbent resin, the solvent is left to remain.

<38>

The method for manufacturing a material for an absorbent article as set forth in any one of clauses <35> to <37>, wherein, when mixing the antimicrobial agent solution with the absorbent resin, the ratio of the antimicrobial agent solution to the absorbent resin is a ratio at which the mass of the organic hydrophobic antimicrobial agent in the antimicrobial agent solution relative to the mass of the absorbent resin is preferably not less than 0.001 mass %, more preferably not less than 0.005 mass %, even more preferably not less than 0.01 mass %, and yet more preferably not less than 0.05 mass %, and the mass of the organic hydrophobic antimicrobial agent in the antimicrobial agent solution is preferably not more than 1 mass %, more preferably not more than 0.7 mass %, and even more preferably not more than 0.5 mass %.

<39>

The method for manufacturing a material for an absorbent article as set forth in any one of clauses <35> to <37>, wherein, when mixing the antimicrobial agent solution with the absorbent resin, the ratio of the antimicrobial agent solution to the absorbent resin is a ratio at which the mass of the organic solvent in the antimicrobial agent solution relative to the mass of the absorbent resin is preferably not less than 0.01 mass %, more preferably not less than 0.02 mass %, even more preferably not less than 0.03 mass %, and yet more preferably not less than 0.05 mass %, and the mass of the organic solvent in the antimicrobial agent solution relative to the mass of the absorbent resin is preferably not more than 10 mass %, more preferably not more than 7 mass %, even more preferably not more than 5 mass %, and yet more preferably not more than 3 mass %.

<40>

The method for manufacturing a material for an absorbent article as set forth in any one of clauses <35> to <39>, wherein, when mixing the antimicrobial agent solution with the absorbent resin, the antimicrobial agent solution may be added to the absorbent resin, the absorbent resin may be added to the antimicrobial agent solution, or the antimicrobial agent solution and the absorbent resin may be mixed at the same time.

<41>

The method for manufacturing a material for an absorbent article as set forth in any one of clauses <35> to <40>, wherein the method comprising a surface-crosslinking step of crosslinking a surface of the absorbent resin prior to the step of mixing the antimicrobial agent solution with the absorbent resin.

<42>

The method for manufacturing a material for an absorbent article as set forth in any one of clauses <35> to <41>, the method further comprising the step of mixing the absorbent resin with inorganic fine particles after mixing the antimicrobial agent solution with the absorbent resin.

<43>

The method for manufacturing a material for an absorbent article as set forth in clause <42>, wherein silica fine particles, zirconia oxide, aluminum oxide, iron oxide, zinc oxide, gold, or the like is used for the inorganic fine particles, and these types of inorganic fine particles are used alone or in combination of two or more.

<44>

The method for manufacturing a material for an absorbent article as set forth in clause <42> or <43>, wherein the inorganic fine particles have an average primary particle size of preferably not less than 5 nm and more preferably not less than 10 nm, and also preferably not more than 500 nm and more preferably not more than 100 nm.

<45>

The method for manufacturing a material for an absorbent article as set forth in any one of clauses <42> to <44>, wherein, when mixing the inorganic fine particles with the absorbent resin that has been mixed with the antimicrobial agent solution, the ratio of the inorganic fine particles to the absorbent resin is such that the mass of the fed inorganic fine particles relative to the mass of the water-absorbent, that is, the absorbent resin prior to being mixed with the antimicrobial agent solution is preferably not less than 0.01 mass %, more preferably not less than 0.05 mass %, even more preferably not less than 0.1 mass %, and yet more preferably not less than 0.2 mass %, and the mass of the inorganic fine particles relative to the mass of the absorbent resin that has been fed is preferably not more than 5 mass %, more preferably not more than 4 mass %, even more preferably not more than 3 mass %, and yet more preferably not more than 2 mass %.

<46>

The method for manufacturing a material for an absorbent article as set forth in any one of clauses <42> to <45>, wherein, when mixing the absorbent resin with the inorganic fine particles after mixing the antimicrobial agent solution with the absorbent resin, the inorganic fine particles may be added to the absorbent resin after being mixed with the antimicrobial agent solution, the absorbent resin after being mixed with the antimicrobial agent solution may be added to the inorganic fine particles, or the inorganic fine particles and the absorbent resin after being mixed with the antimicrobial agent solution may be mixed at the same time.

<47>

The method for manufacturing a material for an absorbent article as set forth in any one of clauses <34> to <46>, wherein the organic hydrophobic antimicrobial agent is an organic compound having a structure represented by formula (1) or (2) below or triclosan:

[Chem. 6]

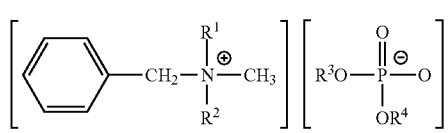

(1)

wherein $R^1$ and $R^2$ each independently represent a methyl group, an ethyl group, a linear or branched alkyl group having 6 to 24 carbon atoms or a linear or branched alkenyl group having 6 to 24 carbon atoms; and
one of $R^3$ and $R^4$ represents a linear or branched alkyl group having 6 to 30 carbon atoms, a linear or branched alkenyl group having 6 to 30 carbon atoms or an alkyl-alkylene oxide group (an alkyl moiety and an alkylene moiety in the group may be linear or may be branched), and the other of $R^3$ and $R^4$ represents a hydrogen atom, a methyl group, or an ethyl group, or alternatively, $R^3$ and $R^4$ each independently represent a linear or branched alkyl group having 6 to 30 carbon atom, a linear or branched alkenyl group having 6 to 30 carbon atoms, or an alkyl-alkylene oxide group (an alkyl moiety and an alkylene moiety in the group may be linear or may be branched),

[Chem. 7]

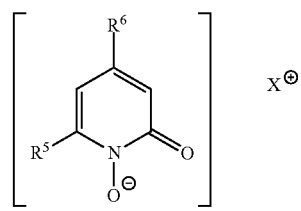

(2)

wherein $R^5$ represents a linear or branched alkyl group having 1 to 30 carbon atoms, a linear or branched alkenyl group having 1 to 30 carbon atoms, an optionally linear or branched cycloalkyl group, an optionally linear or branched aryl group, or an alkyl-alkylene oxide group (an alkyl moiety and an alkylene moiety in the group may be linear or may be branched);
$R^6$ represents a hydrogen atom, a linear or branched alkyl group having 1 to 6 carbon atoms, a linear or branched alkenyl group having 1 to 6 carbon atoms, an optionally linear or branched cycloalkyl group, a phenyl group, or a benzyl group; and
$X^+$ represents an alkali metal ion, an alkaline earth metal ion, an ammonium ion, or a divalent to tetravalent cation (excluding an alkaline earth metal ion).

<48>

The method for manufacturing a material for an absorbent article as set forth in any one of clauses <34> to <47>, wherein the organic hydrophobic antimicrobial agent is benzalkonium cetyl phosphate or piroctone olamine.

<49>

The method for manufacturing a material for an absorbent article as set forth in any one of clauses <34> to <48>, wherein the organic hydrophobic antimicrobial agent has a solubility in water at 25° C. of preferably not more than 40 g, more preferably not more than 10 g, and even more preferably not more than 1 g.

<50>

The method for manufacturing a material for an absorbent article as set forth in any one of clauses <34> to <49>, an organic solvent in which the organic hydrophobic antimicrobial agent has a solubility of preferably not less than 5 mass %, more preferably not less than 10 mass %, and even more preferably not less than 15 mass % is used.

<51>

The method for manufacturing a material for an absorbent article as set forth in any one of clauses <34> to <50>, wherein the organic solvent being hydrophilic means that the organic solvent has a solubility in water at 25° C. of not less than 10 mass %.

<52>

The method for manufacturing a material for an absorbent article as set forth in any one of clauses <34> to <51>, wherein the organic solvent is at least one hydrophilic organic solvent selected from the group consisting of ethylene glycol, propylene glycol, and butylene glycol.

<53>
The method for manufacturing a material for an absorbent article as set forth in any one of clauses <34> to <52>, wherein the organic solvent has a solubility parameter of preferably not less than 12, more preferably not less than 13, even more preferably not less than 13.5, and yet more preferably not less than 14, and also preferably not more than 28, more preferably not more than 27, even more preferably not more than 26, and yet more preferably not more than 25.

<54>
The method for manufacturing a material for an absorbent article as set forth in any one of clauses <34> to <53>, wherein the organic solvent has a vapor pressure at 25° C. of preferably not more than 30 Pa, more preferably not more than 20 Pa, even more preferably not more than 15 Pa, and yet more preferably not more than 10 Pa.

<55>
The method for manufacturing a material for an absorbent article as set forth in any one of clauses <34> to <54>, wherein the organic solvent has a flash point of preferably not less than 100° C., more preferably not less than 105° C., even more preferably not less than 110° C., and yet more preferably not less than 115° C.

<56>
The method for manufacturing a material for an absorbent article as set forth in any one of clauses <34> to <55>, wherein the organic solvent has a viscosity at 25° C. of preferably not less than 5 mPa·s, more preferably not less than 10 mPa·s, even more preferably not less than 30 mPa·s, and yet more preferably not less than 60 mPa·s, and also preferably not more than 1500 mPa·s, more preferably not more than 500 mPa·s, even more preferably not more than 300 mPa·s, and yet more preferably not more than 90 mPa·s.

<57>
The method for manufacturing a material for an absorbent article as set forth in any one of clauses <34> to <56>, wherein the organic solvent is a water-soluble organic solvent such as a polyhydric alcohol including dihydric alcohols (diols), trihydric alcohols (triols), and tetrahydric or higher polyhydric alcohols.

<58>
The method for manufacturing a material for an absorbent article as set forth in clause <57>, wherein the alkyl group of the polyhydric alcohol has preferably 2 or more carbon atoms and also preferably 18 or less carbon atoms, more preferably 10 or less carbon atoms, and even more preferably 4 or less carbon atoms.

<59>
The method for manufacturing a material for an absorbent article as set forth in clause <57> or <58>, wherein the polyhydric alcohol is a lower dihydric alcohol having 2 to 4 carbon atoms,
  the lower dihydric alcohol is at least one hydrophilic organic solvent selected from the group consisting of ethylene glycol, propylene glycol, and butylene glycol,
  the propylene glycol is 1,2-propylene glycol or 1,3-propylene glycol, and
  the butylene glycol is 1,3-butylene glycol, 1,4-butylene glycol, or 2,3-butylene glycol.

<60>
The method for manufacturing a material for an absorbent article as set forth in any one of clauses <34> to <59>, wherein the organic solvent is at least one hydrophilic organic solvent selected from the group consisting of ethylene glycol, propylene glycol, and butylene glycol.

<61>
The method for manufacturing a material for an absorbent article as set forth in clause <60>, wherein the propylene glycol is 1,2-propylene glycol or 1,3-propylene glycol, and
  the butylene glycol is 1,3-butylene glycol, 1,4-butylene glycol, or 2,3-butylene glycol.

<62>
The method for manufacturing a material for an absorbent article as set forth in any one of clauses <34> to <61>, wherein the antimicrobial agent solution contains the organic hydrophobic antimicrobial agent at a concentration of preferably not less than 0.5 mass %, more preferably not less than 1 mass %, even more preferably not less than 3 mass %, and yet more preferably not less than 5 mass %, and also preferably not more than 50 mass %, more preferably not more than 35 mass %, even more preferably not more than 25 mass %, and yet more preferably not more than 20 mass %.

<63>
The method for manufacturing a material for an absorbent article as set forth in clause <34>, the method further comprising the step of making a sheet for an absorbent article contain the antimicrobial agent solution further containing water in an amount of not more than 8 mass %.

<64>
The method for manufacturing a material for an absorbent article as set forth in clause <34>, the method further comprising the step of making a sheet for an absorbent article contain the antimicrobial agent solution further containing water in an amount of not more than 30 mass %, and then drying the sheet.

<65>
The method for manufacturing a material for an absorbent article as set forth in clause <63> or <64>, wherein after the sheet is made to contain the antimicrobial agent solution, the hydrophilic non-volatile organic solvent is left to remain in the sheet.

<66>
The method for manufacturing a material for an absorbent article as set forth in any one of clauses <63> to <65>, wherein the antimicrobial agent solution is applied partially to a sheet through dripping, applied to the entire surface of a sheet through spraying, or applied to a sheet by using various printing methods, or a sheet is immersed in the antimicrobial agent solution.

<67>
The method for manufacturing a material for an absorbent article as set forth in clause <34>, wherein the material for an absorbent article is an absorbent core.

<68>
A method for manufacturing an absorbent article, the method including the step of making an absorbent core contain an antimicrobial agent solution formed by dissolving an organic hydrophobic antimicrobial agent in a hydrophilic non-volatile organic solvent.

<69>
The method for manufacturing an absorbent article as set forth in clause <68>, wherein the organic hydrophobic antimicrobial agent being hydrophobic means that the antimicrobial agent has a solubility in water at 25° C. of not more than 40 g, preferably not more than 10 g, and more preferably not more than 1 g.

<70>
The method for manufacturing an absorbent article as set forth in clause <68> or <69>, wherein the organic solvent being hydrophilic means that the organic solvent has a solubility in water at 25° C. of not less than 10 mass %.

<71>

The method for manufacturing an absorbent article as set forth in any one of clauses <68> to <70>, wherein the organic solvent being non-volatile means that the organic solvent has a vapor pressure at 25° C. of not more than 30 Pa, preferably not more than 20 Pa, more preferably not more than 15 Pa, and even more preferably not more than 10 Pa.

<72>

The method for manufacturing an absorbent article as set forth in any one of clauses <68> to <71>, wherein the antimicrobial agent solution contains water, and the content of water is not more than 8 mass % with respect to the mass of the antimicrobial agent solution.

<73>

The method for manufacturing an absorbent article as set forth in any one of clauses <68> to <72>, wherein after the absorbent core is made to contain the antimicrobial agent solution, the hydrophilic non-volatile organic solvent is left to remain in the absorbent core.

<74>

The method for manufacturing an absorbent article as set forth in any one of clauses <68> to <73>, wherein the organic hydrophobic antimicrobial agent is an organic compound represented by formula (1) or (2) below or triclosan:

[Chem. 8]

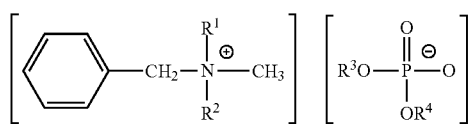

(1)

wherein $R^1$ and $R^2$ each independently represent a methyl group, an ethyl group, a linear or branched alkyl group having 6 to 24 carbon atoms or a linear or branched alkenyl group having 6 to 24 carbon atoms; and one of $R^3$ and $R^4$ represents a linear or branched alkyl group having 6 to 30 carbon atoms, a linear or branched alkenyl group having 6 to 30 carbon atoms or an alkyl-alkylene oxide group (an alkyl moiety and an alkylene moiety in the group may be linear or may be branched), and the other of $R^3$ and $R^4$ represents a hydrogen atom, a methyl group, or an ethyl group, or alternatively, $R^3$ and $R^4$ each independently represent a linear or branched alkyl group having 6 to 30 carbon atom, a linear or branched alkenyl group having 6 to 30 carbon atoms, or an alkyl-alkylene oxide group (an alkyl moiety and an alkylene moiety in the group may be linear or may be branched),

[Chem. 9]

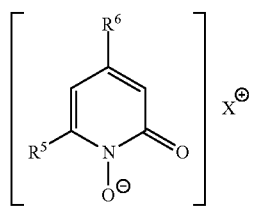

(2)

wherein $R^5$ represents a linear or branched alkyl group having 1 to 30 carbon atoms, a linear or branched alkenyl group having 1 to 30 carbon atoms, an optionally linear or branched cycloalkyl group, an optionally linear or branched aryl group, or an alkyl-alkylene oxide group (an alkyl moiety and an alkylene moiety in the group may be linear or may be branched);

$R^6$ represents a hydrogen atom, a linear or branched alkyl group having 1 to 6 carbon atoms, a linear or branched alkenyl group having 1 to 6 carbon atoms, an optionally linear or branched cycloalkyl group, a phenyl group, or a benzyl group; and $X^+$ represents an alkali metal ion, an alkaline earth metal ion, an ammonium ion, or a divalent to tetravalent cation (excluding an alkaline earth metal ion).

<75>

The method for manufacturing an absorbent article as set forth in any one of clauses <68> to <74>, wherein the hydrophilic non-volatile organic solvent is at least one organic solvent selected from the group consisting of propylene glycol, ethylene glycol, and butylene glycol.

<76>

The method for manufacturing an absorbent article as set forth in any one of clauses <68> to <75>, wherein the antimicrobial agent solution is applied partially to an absorbent core through dripping, applied to the entire surface of an absorbent core through spraying, or applied to an absorbent core by using various printing methods, or an absorbent core is immersed in the antimicrobial agent solution.

<77>

An absorbent article that is manufactured by using to the method for manufacturing an absorbent article as set forth in any one of clauses <68> to <76>.

<78>

A method for manufacturing an absorbent article, the method including the step of pneumatically conveying a material for an absorbent article, the material being manufactured by using the manufacturing method as set forth in any one of clauses <34> to <67>.

<79>

An absorbent article comprising an absorbent core containing an organic hydrophobic antimicrobial agent and a hydrophilic non-volatile organic solvent.

<80>

The absorbent article as set forth in clause <79>, wherein the hydrophobic antimicrobial agent being hydrophobic means that the antimicrobial agent has a solubility in water at 25° C. of not more than 40 g, preferably not more than 10 g, and more preferably not more than 1 g.

<81>

The absorbent article as set forth in clause <79> or <80>, wherein the organic solvent being hydrophilic means that the organic solvent has a solubility in water at 25° C. of not less than 10 mass %.

<82>

The absorbent article as set forth in any one of clauses <79> to <81>, wherein the organic solvent being non-volatile means that the organic solvent has a vapor pressure at 25° C. of not more than 30 Pa, preferably not more than 20 Pa, more preferably not more than 15 Pa, and even more preferably not more than 10 Pa.

<83>

The absorbent article as set forth in any one of clauses <79> to <82>, wherein the absorbent core contains water, and the content of water is preferably not more than 10 mass % with respect to the mass of the absorbent core.

<84>

The absorbent article as set forth in any one of clauses <79> to <83>, wherein the organic hydrophobic antimicrobial agent is present in the absorbent core in an amount of preferably not less than 0.01 g/m², more preferably not less than 0.05 g/m², and even more preferably not less than 0.1 g/m², and also preferably not more than 10.0 g/m², more preferably not more than 5.0 g/m², and even more preferably not more than 2.0 g/m².

<85>

The absorbent article as set forth in any one of clauses <79> to <84>, wherein the organic solvent is present in the absorbent core in an amount of preferably not less than 0.01 g/m², more preferably not less than 0.02 g/m², and even more preferably not less than 0.05 g/m², and also preferably not more than 10 g/m², more preferably not more than 5 g/m², and even more preferably not more than 3 g/m².

<86>

The absorbent article as set forth in any one of clauses <79> to <85>, wherein the ratio between the used amount of the organic hydrophobic antimicrobial agent and the used amount of the organic solvent is such that the mass of the organic solvent is preferably not less than 4 times, more preferably not less than 5 times, and even more preferably not less than 8 times, and also preferably not more than 1000 times, more preferably not more than 100 times, and even more preferably 50 times the mass of the organic hydrophobic antimicrobial agent.

<87>

The absorbent article as set forth in any one of clauses <79> to <86>, wherein the absorbent core is at least one material selected from a mixed fiber stack of fluff pulp and a water-absorbent polymer, a deposit composed of only an absorbent polymer, and a fiber stack composed of only fluff pulp.

<88>

The absorbent article as set forth in any one of clauses <79> to <87>, wherein the organic hydrophobic antimicrobial agent is an organic compound represented by formula (1) or (2) below or triclosan:

[Chem. 10]

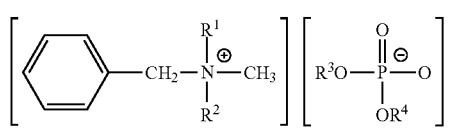

(1)

wherein R¹ and R² each independently represent a methyl group, an ethyl group, a linear or branched alkyl group having 6 to 24 carbon atoms or a linear or branched alkenyl group having 6 to 24 carbon atoms; and one of R³ and R⁴ represents a linear or branched alkyl group having 6 to 30 carbon atoms, a linear or branched alkenyl group having 6 to 30 carbon atoms or an alkyl-alkylene oxide group (an alkyl moiety and an alkylene moiety in the group may be linear or may be branched), and the other of R³ and R⁴ represents a hydrogen atom, a methyl group, or an ethyl group, or alternatively, R³ and R⁴ each independently represent a linear or branched alkyl group having 6 to 30 carbon atom, a linear or branched alkenyl group having 6 to 30 carbon atoms, or an alkyl-alkylene oxide group (an alkyl moiety and an alkylene moiety in the group may be linear or may be branched),

[Chem. 11]

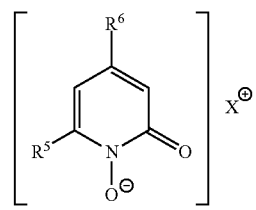

(2)

wherein R⁵ represents a linear or branched alkyl group having 1 to 30 carbon atoms, a linear or branched alkenyl group having 1 to 30 carbon atoms, an optionally linear or branched cycloalkyl group, an optionally linear or branched aryl group, or an alkyl-alkylene oxide group (an alkyl moiety and an alkylene moiety in the group may be linear or may be branched);

R⁶ represents a hydrogen atom, a linear or branched alkyl group having 1 to 6 carbon atoms, a linear or branched alkenyl group having 1 to 6 carbon atoms, an optionally linear or branched cycloalkyl group, a phenyl group, or a benzyl group; and X⁺ represents an alkali metal ion, an alkaline earth metal ion, an ammonium ion, or a divalent to tetravalent cation (excluding an alkaline earth metal ion).

<89>

The absorbent article as set forth in any one of clauses <79> to <88>, wherein the organic hydrophobic antimicrobial agent is benzalkonium cetyl phosphate or piroctone olamine.

<90>

The absorbent article as set forth in any one of clauses <79> to <89>, wherein an organic solvent in which the organic hydrophobic antimicrobial agent can be dissolved is used as the organic solvent, and in particular, the organic solvent in which the organic hydrophobic antimicrobial agent has a solubility of preferably not less than 5 mass %, more preferably not less than 10 mass %, and even more preferably not less than 15 mass % is used.

<91>

The absorbent article as set forth in any one of clauses <79> to <90>, wherein the organic solvent has a solubility parameter of preferably not less than 12, more preferably not less than 13, even more preferably not less than 13.5, and yet more preferably not less than 14, and also preferably not more than 28, more preferably not more than 27, even more preferably not more than 26, and yet more preferably not more than 25.

<92>

The absorbent article as set forth in any one of clauses <79> to <91>, wherein a polyhydric alcohol is used as the organic solvent, a lower dihydric alcohol having 2 to 4 carbon atoms, of polyhydric alcohols, is preferably used, and specifically, at least one hydrophilic organic solvent selected from the group consisting of ethylene glycol, propylene glycol, and butylene glycol is preferably used.

<93>

The absorbent article as set forth in clause <92>, wherein the propylene glycol is at least one selected from the group consisting of 1,2-propylene glycol and 1,3-propylene glycol, and the butylene glycol is at least one selected from the group consisting of 1,3-butylene glycol, 1,4-butylene glycol, and 2,3-butylene glycol.

EXAMPLES

Hereinafter, the present invention will be described in greater detail using examples. However, the scope of the present invention is not limited to the following examples. It should be noted that "%" and "part" as used herein mean "mass %" and "part by mass", unless otherwise specified.

Example 1-1

(1) Preparation of Antimicrobial Solution

An antimicrobial agent solution was prepared using an organic hydrophobic antimicrobial agent and an organic solvent shown in Table 1 below. With regard to the organic hydrophobic antimicrobial agent, piroctone olamine manufactured by Clariant under the trade name "Piroctone Olamine" and benzalkonium cetyl phosphate manufactured by Kao Corporation under the trade name "SANISOL P" were used. With regard to the organic solvent, organic solvents listed below were used:

Ethylene glycol: manufactured by Dow Chemical Japan Limited
Propylene glycol: manufactured by Dow Chemical Japan Limited
1,3-Butylene glycol: manufactured by Daicel Corporation
Glycerin: manufactured by Wako Pure Chemical Industries, Ltd.
Ethanol: manufactured by Wako Pure Chemical Industries, Ltd.
Dimethyl formamide: manufactured by Wako Pure Chemical Industries, Ltd.
Dimethyl sulfoxide: manufactured by Wako Pure Chemical Industries, Ltd.
Polyethylene glycol: "PEG-20" manufactured by Sanyo Chemical Industries, Ltd.

The organic hydrophobic antimicrobial agent was completely dissolved in the organic solvent at 80° C. or higher and then allowed to cool to room temperature (25° C.). The concentration of the organic hydrophobic antimicrobial agent in the antimicrobial agent solution was as shown in Table 1. The organic hydrophobic antimicrobial agent was completely dissolved in the organic solvent.

(2) Provision of Absorbent Resin

"AQUALIC CA" (trade name) manufactured by Nippon Shokubai Co., Ltd. was used as an absorbent resin.

(3) Mixing of Absorbent Resin with Antimicrobial Agent Solution

The antimicrobial agent solution was added to and mixed with the absorbent resin to obtain an absorbent resin composition. The mixing ratio of the antimicrobial agent solution to the absorbent resin was as shown in Table 1. After mixing, no operation for removing the organic solvent was performed. The yields of the organic hydrophobic antimicrobial agent and the organic solvent in the obtained absorbent resin composition were as shown in Table 1.

Examples 1-2 to 1-6

Absorbent resin compositions were obtained in the same manner as in Example 1-1 except that the conditions shown in Table 1 were used.

Examples 1-7 to 1-10

Absorbent resin compositions were obtained by adding amorphous silica (manufactured by Nippon Aerosil Co., Ltd., trade name: "AEROSIL 200", average primary particle size: 12 nm, average BET specific surface area: 200 $m^2/g$) and further mixing after the step (3) in Examples 1-2 and 1-3. The amounts of amorphous silica that were added were as shown in Table 1.

Examples 1-11 and 1-12

An organic hydrophobic antimicrobial agent shown in Table 2 was used. Absorbent resin compositions were obtained in the same manner as in Example 1-1 except that the conditions shown in Table 2 were used.

Examples 1-13 and 1-14

An organic hydrophobic antimicrobial agent shown in Table 2 was used. Absorbent resin compositions were obtained in the same manner as in Example 1-7 except that the conditions shown in Table 2 were used.

Comparative Example 1-1

An organic solvent shown in Table 2 was used. An absorbent resin composition was obtained in the same manner as in Example 1-1 except that the conditions shown in Table 2 were used. In this comparative example, considering possible danger and smell (alcoholic odor), a step of allowing ethanol, which was used as the organic solvent, to be completely removed through volatilization was required in the middle of preparation of the absorbent resin composition.

Comparative Example 1-2

An organic solvent shown in Table 2 was used. Moreover, an organic hydrophobic antimicrobial agent shown in Table 2 was used. Furthermore, an absorbent resin composition was obtained in the same manner as in Example 1-1 except that the conditions shown in Table 2 were used. As in the case of Comparative Example 1, in this comparative example, considering possible danger and smell (alcoholic odor), a step of allowing ethanol, which was used as the organic solvent, to be completely removed through volatilization was required in the middle of preparation of the absorbent resin composition.

Comparative Examples 1-3 and 1-4

Polyethylene glycol was used as the organic solvent, and piroctone olamine (Comparative Example 1-3) or benzalkonium cetyl phosphate (Comparative Example 1-4) was used as the organic hydrophobic antimicrobial agent. Furthermore, absorbent resin compositions were obtained in the same manner as in Example 1-1 except for the conditions shown in the table. In these comparative examples, although preparation of a 10% solution of the organic hydrophobic antimicrobial agent was attempted, the organic hydrophobic antimicrobial agent was not dissolved. Here, in the case where the concentration of the antimicrobial agent is less than 10%, the proportion of the organic solvent is large even if the antimicrobial agent is dissolved, the flowability of the resulting absorbent resin composition is poor, and it is difficult to manufacture an absorbent article that easily exhibits stable absorption performance and antimicrobial performance.

With regard to Comparative Example 1-3, preparation of an absorbent resin composition was abandoned because (1)

yellowing occurred and (2) during mixing with the absorbent resin, the organic hydrophobic antimicrobial agent unevenly adhered to the absorbent resin (stable antimicrobial properties were unable to be reproduced). With regard to Comparative Example 1-4 as well, preparation of an absorbent resin composition was abandoned because, during mixing with the absorbent resin, the organic hydrophobic antimicrobial agent unevenly adhered to the absorbent resin (stable antimicrobial properties were unable to be reproduced). It should be noted that "adhering unevenly" means a phenomenon in which, when a liquid in which an organic hydrophobic antimicrobial agent is insoluble is added to an absorbent resin, the organic hydrophobic antimicrobial agent cannot be uniformly spread due to clogging of a spray hole. If the organic hydrophobic antimicrobial agent unevenly adheres to the absorbent resin, a portion of the absorbent resin composition in which the amount of antimicrobial agent that adheres to the absorbent resin is small and a portion of the absorbent resin composition in which a set amount of antimicrobial agent adheres to the water-absorbent amount coexist. A desired antimicrobial effect cannot be obtained in the portion of the absorbent resin composition in which the amount of antimicrobial agent that adheres to the absorbent resin is small. Therefore, the absorbent article as a whole cannot have an antimicrobial effect equivalent to those of the examples.

Comparative Examples 1-5 and 1-6

Piroctone olamine was used as the organic hydrophobic antimicrobial agent, and dimethylformamide (Comparative Example 1-5) or dimethylsulfoxide (Comparative Example 1-6) was used as the organic solvent. Preparation of a 10% solution of the organic hydrophobic antimicrobial agent was attempted. In Comparative Example 1-5, the organic hydrophobic antimicrobial agent was not dissolved. Therefore, in Comparative Example 1-5 as well, the organic hydrophobic antimicrobial agent unevenly adhered to the absorbent resin, and thus, an antimicrobial effect equivalent to those of the examples could not be obtained. Moreover, an amine odor derived from the solvent was generated. Thus, preparation of an absorbent resin composition was abandoned. On the other hand, in Comparative Example 1-6, although the organic hydrophobic antimicrobial agent was dissolved, a sulfurous odor derived from the solvent was generated. Thus, preparation of an absorbent resin composition was abandoned.

Evaluation

The antimicrobial effect of each of the absorbent resin compositions obtained in the examples and the comparative examples (except for Comparative Examples 1-3 to 1-6) was measured and evaluated based on antimicrobial properties as will be described below. Moreover, the angle of repose and the angle of spatula, the angle of fall, the loose apparent specific gravity, and the compressibility were measured with a Powder Tester PT-R manufactured by Hosokawa Micron Corporation by using the above-described methods. Moreover, the coverage of the surface of the absorbent resin by the antimicrobial agent was measured. Furthermore, as described below, the absorption performance of the absorbent resin was measured and evaluated based on a saturated absorption amount. Tables 1 and 2 show the results. It should be noted that Table 2 also shows reference examples (examples in which no antimicrobial agent was used).

Evaluation of Saturated Absorption Amount

A woven fabric (mesh opening 255) made from nylon was cut into a rectangular shape having a width of 10 cm and a length of 40 cm, folded in two at its middle with respect to the longitudinal direction, and heat-sealed at both ends to produce a nylon bag having a width of 10 cm (internal size of 9 cm) and a length of 20 cm. Then, 0.50 g of an absorbent resin composition serving as a measurement specimen was accurately weighed and uniformly placed in a bottom portion of the produced nylon bag. The nylon bag in which the specimen was placed was immersed in a physiological saline solution (0.9% aqueous solution of sodium chloride) whose temperature was adjusted to 25° C. After 30 minutes elapsed from the start of immersion, the nylon bag was removed from the physiological saline solution and drained by vertically suspending the nylon bag for one hour. Then, measurement of the mass was performed, and the saturated absorption amount to be obtained was calculated in accordance with an equation below:

$$\text{Saturated absorption amount (g/g)} = (a-b-c)/c$$

wherein "a" indicates the total mass (g) of the absorbent resin composition and the nylon bag after draining, "b" indicates the mass (g) of the nylon bag before absorbing water (while dry), and "c" indicates the mass (g) of the absorbent resin composition before absorbing water (0.50). The measurement was performed three times, and an average value was used as the measurement value. It should be noted that the measurement was performed at 23±2° C. and a humidity of 50±5% RH.

Evaluation of Antimicrobial Properties (1) Strain and Human Urine Used

For the evaluation of the antimicrobial properties, a colon *bacillus* (16S identified through rDNA partial sequence analysis) collected from a used (only urination) disposable diaper and isolated was used. Moreover, equal amounts of human urine collected from two healthy men were mixed together, the mixture was filtrated and sterilized by using a 0.2 μm filter (Thermo Fisher Scientific Inc., trade name "Nalgene, tissue culture unit"), and the filtrate was used as human urine. It should be noted that after the above-described strain was inoculated into the human urine and cultured, generation of a noticeable odor was recognized.

(2) Evaluation of Antimicrobial Properties

The colon *bacillus* strain was cultured overnight in an SCD agar plate medium. The obtained colonies were collected by scraping a plurality of times with a sterile loop. The collected colonies were suspended in a physiological saline solution to prepare a bacterial suspension having a concentration on the order of $10^9$ in terms of CFU/mL. The obtained bacterial suspension was added to the human urine in an amount of 1 v/v % to obtain bacterium-added urine. Then, 30 mg of each absorbent resin composition (sample) or an untreated absorbent resin (control) was placed into a 1.5 mLμ test tube. Subsequently, 900 μL of the bacterium-added urine was added to the test tube, and the test tube was allowed to stand in a thermostatic chamber at 37° C.

After 24 hours, the content was taken out by washing with 8.1 mL of an LP diluent. Extraction by shaking was performed by using a high-speed shaking device (EYELA, CUTE MIXER CM-1000) at 1500 rpm for 15 minutes. The obtained extract was diluted as appropriate with an LP diluent, smeared on an SCDLP agar plate medium, and cultured overnight in a thermostatic chamber at 37° C. Then, the number of colonies was counted. Thus, the CFU of the samples and the control was calculated, and the antimicrobial activity values of the respective samples were obtained by using an equation below:

$$\text{Antimicrobial activity value} = \text{Log } 10((\text{CFU of control})/(\text{CFU of sample}))$$

TABLE 1

|  |  | Ex. 1-1 | Ex. 1-2 | Ex. 1-3 | Ex. 1-4 | Ex. 1-5 | Ex. 1-6 |
| --- | --- | --- | --- | --- | --- | --- | --- |
| Organic hydrophobic antimicrobial agent |  | Piroctone olamine | Piroctone olamine | Piroctone olamine | Piroctone olamine | Piroctone olamine | Piroctone olamine |
| Amount added (relative to absorbent resin) | % | 0.1 | 0.1 | 0.1 | 0.1 | 0.05 | 0.025 |
| Yield (relative to amount added) | % | 100 | 100 | 100 | 100 | 100 | 100 |
| Organic solvent |  | Ethylene glycol | Propylene glycol | 1,3-Butylene glycol | Glycerin | Propylene glycol | Propylene glycol |
| Concentration of antimicrobial agent | % | 10 | 10 | 10 | 10 | 10 | 10 |
| Amount added (relative to absorbent resin) | % | 1 | 1 | 1 | 1 | 0.5 | 0.25 |
| Yield (relative to amount added) |  | 100 | 100 | 100 | 100 | 100 | 100 |
| Inorganic fine particles |  | None | None | None | None | None | None |
| Amount added (relative to absorbent resin) | % | 0 | 0 | 0 | 0 | 0 | 0 |
| Saturated absorption amount | g/g | 57 | 56 | 56 | 58 | 57 | 58 |
| Antimicrobial properties |  | 2.3 | 3.0 | 2.4 | 2.1 | 1.9 | 1.4 |
| Angle of repose | Degrees | 44 | 44 | 44 | 45 | 42 | 40 |
| Angle of spatula | Degrees | 53 | 57 | 51 | 57 | 52 | 49 |
| Angle of fall | Degrees | 42 | 42 | 43 | 43 | 40 | 39 |
| Loose apparent specific gravity | g/mL | 0.56 | 0.56 | 0.56 | 0.56 | 0.64 | 0.68 |
| Compressibility | % | 21 | 20 | 21 | 21 | 15 | 10 |
| Coverage by antimicrobial agent | % | 7 | 7 | 10 | 15 | 10 | 10 |

|  |  | Ex. 1-7 | Ex. 1-8 | Ex. 1-9 | Ex. 1-10 |
| --- | --- | --- | --- | --- | --- |
| Organic hydrophobic antimicrobial agent |  | Piroctone olamine | Piroctone olamine | Piroctone olamine | Piroctone olamine |
| Amount added (relative to absorbent resin) | % | 0.1 | 0.1 | 0.1 | 0.1 |
| Yield (relative to amount added) | % | 100 | 100 | 100 | 100 |
| Organic solvent |  | Propylene glycol | 1,3-Butylene glycol | 1,3-Butylene glycol | 1,3-Butylene glycol |
| Concentration of antimicrobial agent | % | 10 | 10 | 10 | 10 |
| Amount added (relative to absorbent resin) | % | 1 | 1 | 1 | 1 |
| Yield (relative to amount added) |  | 100 | 100 | 100 | 100 |
| Inorganic fine particles |  | Amorphous silica | Amorphous silica | Amorphous silica | Amorphous silica |
| Amount added (relative to absorbent resin) | % | 0.5 | 0.5 | 0.3 | 0.7 |
| Saturated absorption amount | g/g | 58 | 58 | 58 | 58 |
| Antimicrobial properties |  | 3.1 | 2.4 | 2.3 | 2.3 |
| Angle of repose | Degrees | 39 | 38 | 37 | 39 |
| Angle of spatula | Degrees | 49 | 45 | 49 | 50 |
| Angle of fall | Degrees | 37 | 36 | 36 | 36 |
| Loose apparent specific gravity | g/mL | 0.67 | 0.68 | 0.68 | 0.68 |
| Compressibility | % | 10 | 11 | 10 | 11 |
| Coverage by antimicrobial agent | % | 25 | 20 | 17 | 23 |

TABLE 2

|  |  | Ex. 1-11 | Ex. 1-12 | Ex. 1-13 | Ex. 1-14 | Com. Ex. 1-1 | Com. Ex. 1-2 | Ref. Ex. |
| --- | --- | --- | --- | --- | --- | --- | --- | --- |
| Organic hydrophobic antimicrobial agent |  | Benzalkonium cetyl phosphate | Benzalkonium cetyl phosphate | Benzalkonium cetyl phosphate | Benzalkonium cetyl phosphate | Piroctone olamine | Benzalkonium cetyl phosphate | None |
| Amount added (relative to absorbent resin) | % | 0.33 | 0.33 | 0.33 | 0.33 | 0.1 | 0.33 | 0 |
| Yield (relative to amount added) | % | 100 | 100 | 100 | 100 | 100 | 100 | — |
| Organic solvent |  | Propylene glycol | 1,3-Butylene glycol | Propylene glycol | 1,3-Butylene glycol | Ethanol | Ethanol | None |
| Concentration of antimicrobial agent | % | 10 | 10 | 10 | 10 | 10 | 10 | — |

TABLE 2-continued

|  |  | Ex. 1-11 | Ex. 1-12 | Ex. 1-13 | Ex. 1-14 | Com. Ex. 1-1 | Com. Ex. 1-2 | Ref. Ex. |
|---|---|---|---|---|---|---|---|---|
| Amount added (relative to absorbent resin) | % | 3.3 | 3.3 | 3.3 | 3.3 | 1 | 3.3 | 0 |
| Yield (relative to amount added) |  | 100 | 100 | 100 | 100 | 0 | 0 | — |
| Inorganic particles |  | None | None | Amorphous silica | Amorphous silica | None | None | None |
| Amount added (relative to absorbent resin) | % | 0 | 0 | 1 | 1 | 0 | 0 | 0 |
| Saturated absorption amount | g/g | 57 | 58 | 57 | 58 | 56 | 54 | 57 |
| Antimicrobial properties |  | 2.1 | 2.1 | 2.3 | 2.3 | 2.0 | 2.0 | 0.0 |
| Angle of repose | Degrees | 50 | 50 | 39 | 39 | 39 | 39 | 39 |
| Angle of spatula | Degrees | 56 | 56 | 52 | 52 | 47 | 49 | 47 |
| Angle of fall | Degrees | 50 | 50 | 36 | 36 | 36 | 37 | 37 |
| Loose apparent specific gravity | g/mL | 0.46 | 0.46 | 0.67 | 0.68 | 0.70 | 0.71 | 0.71 |
| Compressibility | % | 39 | 39 | 14 | 14 | 8 | 9 | 8 |
| Coverage by antimicrobial agent | % | 12 | 12 | 28 | 30 | 2 | 3 | 0 |

As is clear from the results shown in Tables 1 and 2, it can be seen that with respect to the absorbent resin compositions obtained in the examples, the absorption performance was not impaired even though the organic solvent was not removed, and the antimicrobial properties were improved. Moreover, it can be seen that the powder flowability was improved. In contrast, with respect to the absorbent resin compositions of Comparative Examples 1-1 and 1-2, removal of the organic solvent was necessary, and it was required to give consideration to the complexity and safety of manufacturing.

It should be noted that although not shown in the tables, in Comparative Examples 1-3 and 1-4, since the organic hydrophobic antimicrobial agent was not dissolved in the organic solvent, there was a risk that clogging of a spray hole might occur, making uniform spreading impossible. Moreover, there were drawbacks such as yellowing of the solution and the generation of an abnormal odor.

Example 2-1

1) Production of Sheet for Absorbent Article

A piece of tissue paper having a basis weight of 16 g/m², a width of 200 mm, and a length of 170 mm was made to contain an antimicrobial agent solution (piroctone olamine: 1%, propylene glycol: 99%) containing an organic hydrophobic antimicrobial agent, an organic solvent, and water in an amount of not more than 8% by dripping the antimicrobial agent solution onto two portions of the piece of tissue paper in an amount of 0.1 g per portion using a dripper. The positions of the two portions at which the antimicrobial agent solution was contained were set at the two positions located on a center line parallel to the length direction and spaced apart from the midpoint of the center line by respective distances of 30 mm. The types of the organic hydrophobic antimicrobial agent and the organic solvent as well as the total amount added to the piece of tissue paper were as shown in Table 3. In Table 3, "PG" denotes "1,2-propylene glycol". "BG" denotes "1,3-butylene glycol". Moreover, "gsm" denotes "g/m²".

2) Production of Absorbent Member

An absorbent member was manufactured by covering an absorbent core with the sheet for an absorbent article. The absorbent core was made of a mixed fiber stack of fluff pulp having a basis weight of 180 g/m² and a superabsorbent polymer having a basis weight 160 g/m², and had a size of 190 mm in length×70 mm in width and a mass of 5.0 g.

Example 2-2

The antimicrobial agent solution was contained at four positions individually located on the center line parallel to the length direction and spaced apart from the midpoint of the centerline by respectively corresponding distances of 20 mm or 60 mm. The types of the organic hydrophobic antimicrobial agent and the organic solvent as well as the total amount added to the piece of tissue paper were as shown in Table 3. Otherwise, the same procedures as in Example 2-1 were performed.

Example 2-3

1) Preparation of Sheet for Absorbent Article

A piece of tissue paper (200 mm in width×170 mm in length) that was similar to the piece of tissue paper used in Example 2-1 was used.

2) Production of Absorbent Member

An absorbent core made of a mixed fiber stack of fluff pulp having a basis weight of 180 g/m² and a superabsorbent polymer having a basis weight of 160 g/m² was produced. The absorbent core had a size of 190 mm in length×70 mm in width and a mass of 5.0 g. The absorbent core was made to contain an antimicrobial agent solution containing an organic hydrophobic antimicrobial agent, an organic solvent, and water in an amount of not more than 10% by dripping the antimicrobial agent solution onto the absorbent core. The antimicrobial agent solution was contained at one position located on a center line parallel to the length direction on a skin-facing surface of the absorbent core and at the midpoint of that center line. The types of the organic hydrophobic antimicrobial agent and the organic solvent as well as the total amount added to the absorbent core were as shown in Table 3. An absorbent member was manufactured by covering the absorbent core with the sheet for an absorbent article prepared in 1).

Example 2-4

The antimicrobial agent solution was contained at one position located on a central line parallel to the length direction on a skin-facing surface of the absorbent core and at the midpoint of that central line. The types of the organic hydrophobic antimicrobial agent and the organic solvent as well as the total amount added to the piece of tissue paper were as shown in Table 3. Otherwise, the same procedures as in Example 2-1 were performed.

Example 2-5

The types of the organic hydrophobic antimicrobial agent and the organic solvent as well as the total amount added to the tissue paper were as shown in Table 3. Otherwise, the same procedures as in Example 2-4 were performed.

Example 2-6

A piece of tissue paper having a basis weight of 16 g/m², a width of 200 mm, and a length of 170 mm was made to absorb an antimicrobial agent solution (piroctone olamine: 10%, propylene glycol: 70%, ion exchanged water: 20%) containing an organic hydrophobic antimicrobial agent, an organic solvent, and water in an amount of not more than 30% by dripping the antimicrobial agent solution onto two portions of the piece of tissue paper in an amount of 0.1 g per portion with a dripper. Then, the piece of tissue paper was placed in an air dryer that was set at 105° C., and dried for 30 minutes. The positions of the two portions where antimicrobial agent solution was contained were set at the two positions located on a center line parallel to the length direction and spaced apart from the midpoint of that center line by respective distances of 30 mm. The types of the organic hydrophobic antimicrobial agent and the organic solvent as well as the total amount added to the piece of tissue paper were as shown in Table 3.
2) Production of Absorbent Member
An absorbent member was manufactured by covering an absorbent core with the sheet for an absorbent article. The absorbent core was made of a mixed fiber stack of fluff pulp having a basis weight of 180 g/m² and a superabsorbent polymer having a basis weight of 160 g/m², and had a size of 190 mm in length×70 mm in width and a mass of 5.0 g.

Example 2-7

The types of the organic hydrophobic antimicrobial agent and the organic solvent as well as the total amount added to the piece of tissue paper were as shown in Table 3. Otherwise, the same procedures as in Example 2-1 were performed.

Example 2-8

1) Preparation of Sheet for Absorbent Article
A piece of tissue paper (200 mm in width×170 mm in length) that was similar to the piece of tissue paper used in Example 2-1 was used.
2) Production of Absorbent Member
An absorbent core made of a mixed fiber stack of fluff pulp having a basis weight of 180 g/m² and a superabsorbent polymer having a basis weight of 160 g/m² was produced. The absorbent core had a size of 190 mm in length×70 mm in width and a mass of 5.0 g. The absorbent core was made to contain an antimicrobial agent solution containing an organic hydrophobic antimicrobial agent, an organic solvent, and water in an amount of not more than 10%. The antimicrobial agent solution was contained at a position located on a center line parallel to the length direction on a skin-facing surface of the absorbent core and at the midpoint of that center line. The types of the organic hydrophobic antimicrobial agent and the organic solvent as well as the total amount added to the absorbent core were as shown in Table 3. An absorbent member was manufactured by covering the absorbent core with the sheet for an absorbent article prepared in 1).

Example 2-9

1) Preparation of Sheet for Absorbent Article
A piece of tissue paper (200 mm in width×170 mm in length) similar to the piece of tissue paper used in Example 2-1 was used.
2) Production of Absorbent Member
An absorbent core made of a mixed fiber stack of fluff pulp having a basis weight of 180 g/m² and a superabsorbent polymer having a basis weight of 160 g/m² was produced. The absorbent core had a size of 190 mm in length×70 mm in width and a mass of 5.0 g. The absorbent core was made to contain an antimicrobial agent solution including an organic hydrophobic antimicrobial agent, an organic solvent, and water in an amount of not more than 10%. The antimicrobial agent solution was contained at four positions individually located on a center line parallel to the length direction on a skin-facing surface of the absorbent core and spaced apart from the midpoint of the center line by respectively corresponding distances of 20 mm or 60 mm. The types of the organic hydrophobic antimicrobial agent and the organic solvent as well as the total amount added to the absorbent core were as shown in Table 3. An absorbent member was manufactured by covering the absorbent core with the sheet for an absorbent article prepared in 1).

Comparative Example 2-1

This comparative example is an example in which the piece of tissue paper in Example 2-1 was not made to contain the antimicrobial agent solution and used as a sheet for an absorbent article. Otherwise, the same procedures as in Example 2-1 were performed.

Comparative Example 2-2

1) Production of Sheet for Absorbent Article
An organic hydrophobic antimicrobial agent was spread onto a piece of tissue paper having a width of 200 mm and a length of 170 mm. Then, a spray glue was sprayed thereon to immobilize the antimicrobial agent. The organic hydrophobic antimicrobial agent was spread at one position located on a center line parallel to the length direction and at the midpoint of that center line. The type of the organic hydrophobic antimicrobial agent and the amount added to the piece of tissue paper were as shown in Table 3.
2) Production of Absorbent Member
An absorbent member was manufactured by covering an absorbent core with the sheet for an absorbent article. The absorbent core was made of a mixed fiber stack of fluff pulp having a basis weight of 180 g/m² and a superabsorbent polymer having a basis weight of 160 g/m² and had a size of 190 mm in length×70 mm in width and a mass of 5.0 g.

Comparative Example 2-3

1) Preparation of Sheet for Absorbent Article
A piece of tissue paper (200 mm in width×170 mm in length) similar to the piece of tissue paper used in Example 2-1 was used.

2) Production of Absorbent Member

An absorbent core made of a mixed fiber stack of fluff pulp having a basis weight of 180 g/m² and a superabsorbent polymer having a basis weight of 160 g/m² was produced. The absorbent core had a size of 190 mm in length×70 mm in width and a mass of 5.0 g. An organic hydrophobic antimicrobial agent was spread onto the absorbent core, and then, a spray glue was sprayed thereon to immobilize the antimicrobial agent. The organic hydrophobic antimicrobial agent was spread at one position on a center line parallel to the length direction and at the midpoint of that center line. The type of the organic hydrophobic antimicrobial agent and the amount added to the absorbent core were as shown in Table 3. An absorbent member was manufactured by covering the absorbent core with the sheet for an absorbent article prepared in 1).

Comparative Example 2-4

An organic hydrophobic antimicrobial agent was spread onto a piece of tissue paper having a width of 200 mm and a length of 170 mm. Then, a spray glue was sprayed thereon to immobilize the antimicrobial agent. The organic hydrophobic antimicrobial agent was spread at four positions individually located on a center line parallel to the length direction and spaced apart from the midpoint of that center line by respectively corresponding distances of 20 mm or 60 mm. The type of the organic hydrophobic antimicrobial agent and the amount added to the piece of tissue paper were as shown in Table 3. Otherwise, the same procedures as in Comparative Example 2-2 were performed.

Comparative Example 2-5

The type of the organic hydrophobic antimicrobial agent and the amount added to the piece of tissue paper were as shown in Table 3. Otherwise, the same procedures as in Comparative Example 2-2 were performed.

Evaluation

Sensory evaluation of the absorbent members obtained in the examples and comparative examples with respect to the suppression of urine odor was performed in accordance with the following procedures. Table 3 shows the results.

Sensory Evaluation with Respect to Suppression of Urine Odor

<A> Urine to be used for evaluation was prepared in accordance with the procedures (a) to (d) below.

(a) Nonwoven fabrics (not subjected to specific treatment such as antimicrobial treatment and deodorization treatment, size: 10 cm×15 cm) having a basis weight of 20 g/m² were prepared.

(b) Four monitors (adult men in a state in which after 12 hours had elapsed from bathing) each wiped the lower half of their own body thoroughly with the nonwoven fabrics in (a) that were appropriately wetted with water, and thus, resident bacteria on the skin and enteric bacteria derived from feces were collected.

(c) Urine was collected from each of the four monitors. 2.0 g of urine was made to adhere to the nonwoven fabrics in (b). The nonwoven fabrics were each placed and sealed in a plastic bag, and allowed to stand in an atmosphere at 36° C. for 24 hours. Thus, the bacteria on the nonwoven fabrics in (b) were grown.

(d) After that, 500 g of urine collected from each of the monitors was mixed together, and 2000 g of the mixed urine was placed in an Erlenmeyer flask equipped with a stopper. The four nonwoven fabrics (c) on which the bacteria were grown were placed in the flask, the nonwoven fabrics were immersed in the mixed urine for 20 minutes while being stirred at intervals.

<B> Next, 50 g of the urine obtained as a result of (d) was gradually injected into a central portion of each of the absorbent members obtained in the examples and comparative examples. The absorbent members into which the urine was injected were placed and sealed in respective containers each constituted by a deep-type stainless steel tray No. 3 with a lid (manufactured by AS ONE Corporation). The containers were stored in a thermostatic dryer and allowed to stand for 6 hours while being kept warm at 36° C.

After 6 hours had elapsed, the containers were taken out of the thermostatic dryer. Five monitors (adult men and women) different from the above-described monitors performed sensory evaluation based on the criteria below. Specifically, the sensory evaluation was performed in the following manner. First, each container was taken out of the thermostatic dryer. The lid was opened, and the container was allowed to stand for 30 seconds. Then, the monitors brought their nose near to the container and smelled the odors. The monitors evaluated the odors based on the following criteria assuming that the odor of Comparative Example 1 was rated at 5. An average value and a median value of the obtained numerical values were calculated and used as the results of sensory evaluation of each absorbent member.

5: Strong putrid odor
4: Weak putrid odor
3: Strong odor easily recognized as urine
2: Weak odor recognized as urine
1: Slight odor that is hard to determine as urine
0: No odor

TABLE 3

| | | Examples | | | | | | |
|---|---|---|---|---|---|---|---|---|
| | | 2-1 | 2-2 | 2-3 | 2-4 | 2-5 | 2-6 | 2-7 |
| Member to which antimicrobial agent was applied | Sheet for absorbent article | + | + | − | + | + | + | + |
| | Absorbent core made of mixed fiber stack Pulp 180 gsm Absorbent polymer 160 gsm | − | − | + | − | − | − | − |
| Amount of antimicrobial agent solution added | Octopirox/PG (1%/99%) | 0.2 g | 0.4 g | 0.2 g | − | − | − | − |
| | Octopirox/PG (10%/90%) | − | − | − | 0.02 g | − | − | − |
| | Octopirox/PG (30%/70%) | − | − | − | − | 0.0067 g | − | − |
| | Octopirox/PG/ion exchanged water (10%/70%/20%) | − | − | − | − | − | 0.02 g | − |

TABLE 3-continued

|  |  | 2-1 | 2-2 | 2-3 | 2-4 | 2-5 | 2-6 | 2-7 |
|---|---|---|---|---|---|---|---|---|
|  | Octopirox/BG (1%/99%) | – | – | – | – | – | – | 0.2 g |
|  | Triclosan/PG (1%/99%) | – | – | – | – | – | – | – |
|  | Octopirox was applied, and then immobilized with spray glue | – | – | – | – | – | – | – |
|  | Triclosan was applied, and then immobilized with spray glue | – | – | – | – | – | – | – |
|  | Portion(s) of addition | 2 portions | 4 portions | 1 portion | 1 portion | 1 portion | 1 portion | 2 portions |
|  | Moisture content (%) | 10 | 10 | 10 | 8 | 8 | 10 | 10 |
|  | Antimicrobial agent's basis weight (gsm) | 0.06 | 0.12 | 0.15 | 0.06 | 0.06 | 0.06 | 0.06 |
|  | Configuration of absorbent core |  |  |  | Mixed fiber stack |  |  |  |
|  | Sensory evaluation with respect to suppression of urine odor (average value) | 2.0 | 1.6 | 2.0 | 2.0 | 2.0 | 1.9 | 1.9 |
|  | Sensory evaluation with respect to suppression of urine odor (mean value) | 2.0 | 1.5 | 2.0 | 2.0 | 2.0 | 2.0 | 2.0 |

|  |  | Examples | | Comparative Examples | | | | |
|---|---|---|---|---|---|---|---|---|
|  |  | 2-8 | 2-9 | 2-1 | 2-2 | 2-3 | 2-4 | 2-5 |
| Member to which antimicrobial agent was applied | Sheet for absorbent article | – | – | – | + | – | + | + |
|  | Absorbent core made of mixed fiber stack | + | + | – | – | + | – | – |
|  | Pulp 180 gsm |  |  |  |  |  |  |  |
|  | Absorbent polymer 160 gsm |  |  |  |  |  |  |  |
| Amount of antimicrobial agent solution added | Octopirox/PG (1%/99%) | – | – | – | – | – | – | – |
|  | Octopirox/PG (10%/90%) | – | – | – | – | – | – | – |
|  | Octopirox/PG (30%/70%) | – | – | – | – | – | – | – |
|  | Octopirox/PG/ion exchanged water (10%/70%/20%) | – | – | – | – | – | – | – |
|  | Octopirox/BG (1%/99%) | – | – | – | – | – | – | – |
|  | Triclosan/PG (1%/99%) | 0.2 g | 0.4 g | – | – | – | – | – |
|  | Octopirox was applied, and then immobilized with spray glue | – | – | – | 4 mg | 4 mg | 4 mg | – |
|  | Triclosan was applied, and then immobilized with spray glue | – | – | – | – | – | – | 4 mg |
|  | Portion(s) of addition | 1 portion | 4 portions | – | 1 portion | 1 portion | 4 portions | 1 portion |
|  | Moisture content (%) | 10 | 10 | 10 | 10 | 10 | 10 | 10 |
|  | Antimicrobial agent's basis weight (gsm) | 0.15 | 0.30 | – | 0.12 | 0.30 | 0.12 | 0.12 |
|  | Configuration of absorbent core |  |  |  | Mixed fiber stack |  |  |  |
|  | Sensory evaluation with respect to suppression of urine odor (average value) | 1.9 | 1.9 | 5.0 | 4.0 | 3.9 | 3.4 | 3.9 |
|  | Sensory evaluation with respect to suppression of urine odor (mean value) | 2.0 | 2.0 | 5.0 | 4.0 | 4.0 | 3.5 | 4.0 |

In this table, "+" means that an antimicrobial agent solution was added, and "–" means that nothing was added.

As is clear from the results shown in Table 3, it can be seen that the absorbent members obtained in the examples had a higher urine odor suppression effect than the absorbent members of the comparative examples as a result of the antimicrobial agents exhibiting a sufficient antimicrobial effect.

INDUSTRIAL APPLICABILITY

As described in detail above, according to the present invention, a material for an absorbent article, the material having high antimicrobial properties, and an absorbent article having high antimicrobial properties, is provided. Moreover, according to the present invention, a material for an absorbent article, the material having high antimicrobial properties, and an absorbent article having high antimicrobial properties can be easily manufactured. In particular, according to the present invention, an absorbent resin composition having high water absorption performance, generating no odor, and exhibiting a sufficient antimicrobial effect is provided. Furthermore, according to the present invention, an absorbent resin composition that does not impair the water absorption performance of an absorbent resin, generates no odor of its own, and exhibits a sufficient antimicrobial effect can be easily manufactured.

The invention claimed is:

1. A material for an absorbent article, wherein the material comprises a sheet for an absorbent article,
   the sheet containing (a) an organic hydrophobic antimicrobial agent, (b) a hydrophilic non-volatile organic solvent, said organic solvent being at least one member selected from the group consisting of ethylene glycol, propylene glycol, and butylene glycol, and (c) water in an amount of 8 to 10 mass %,
   the sheet for an absorbent article comprises a substrate sheet, and the substrate sheet is a fiber sheet or a perforated sheet in which a plurality of through-holes are formed in a film.

2. A material for an absorbent article, the material comprising:
   an organic hydrophobic antimicrobial agent;
   a hydrophilic non-volatile organic solvent, said organic solvent being at least one member selected from the group consisting of ethylene glycol, propylene glycol, and butylene glycol; and an absorbent core,
wherein the absorbent core contains pulp fibers, and the organic hydrophobic microbial agent and the organic solvent adhere to the absorbent core; and
the material for an absorbent article contains water in an amount of 8 to 10 mass %.

3. The material for an absorbent article according to claim 1 or claim 2,
wherein the organic hydrophobic antimicrobial agent is benzalkonium cetyl phosphate or piroctone olamine.

4. The material for an absorbent article according to claim 3, wherein the material comprises a water-absorbent resin composition including the organic hydrophobic antimicrobial agent, the hydrophilic non-volatile organic solvent, and a water-absorbent resin.

5. The material for an absorbent article according to claim 4, wherein the organic hydrophobic antimicrobial agent and the organic solvent discontinuously adhere to a surface of the water-absorbent resin.

* * * * *